US008932841B2

(12) United States Patent
Atkinson et al.

(10) Patent No.: US 8,932,841 B2
(45) Date of Patent: Jan. 13, 2015

(54) THERMOPHILIC MICROORGANISMS FOR ETHANOL PRODUCTION

(75) Inventors: Anthony Atkinson, Guildford (GB); Roger Cripps, Guildford (GB); Brian Rudd, Welwyn Garden City (GB); Kirstin Eley, Guildford (GB); Steve Martin, Guildford (GB); Paul Milner, Guildford (GB); Claire Mercier, Guildford (GB)

(73) Assignee: TMO Renewables Limited, Guildford (GB)

( * ) Notice: Subject to any disclaimer, the term of this patent is extended or adjusted under 35 U.S.C. 154(b) by 803 days.

(21) Appl. No.: 12/376,826

(22) PCT Filed: Sep. 28, 2007

(86) PCT No.: PCT/GB2007/003699
§ 371 (c)(1),
(2), (4) Date: May 22, 2009

(87) PCT Pub. No.: WO2008/038019
PCT Pub. Date: Apr. 3, 2008

(65) Prior Publication Data
US 2010/0173373 A1 Jul. 8, 2010

(30) Foreign Application Priority Data

Sep. 28, 2006 (GB) .................................. 0619162.1
Nov. 27, 2006 (GB) .................................. 0623570.9

(51) Int. Cl.
*C12P 7/06* (2006.01)
*C12N 1/00* (2006.01)
*C12N 1/20* (2006.01)
*C12N 15/74* (2006.01)
*A23C 9/12* (2006.01)
*C12N 9/10* (2006.01)
*C12N 9/04* (2006.01)
*C12N 9/02* (2006.01)

(52) U.S. Cl.
CPC ............ *C12N 9/1029* (2013.01); *C12N 9/0006* (2013.01); *C12N 9/0008* (2013.01); *C12P 7/065* (2013.01); *Y02E 50/17* (2013.01)
USPC ... 435/161; 435/243; 435/252.3; 435/252.31; 435/471; 426/61

(58) Field of Classification Search
CPC ...................................................... C12N 9/1252
USPC ................. 435/161, 243, 252.3, 252.31, 471; 426/61
See application file for complete search history.

(56) References Cited

U.S. PATENT DOCUMENTS

| | | | |
|---|---|---|---|
| 5,182,199 A * | 1/1993 | Hartley | 435/162 |
| 5,238,833 A | 8/1993 | Sanders et al. | |
| 5,482,846 A * | 1/1996 | Ingram et al. | 435/161 |
| 5,589,369 A | 12/1996 | Seidman et al. | |
| 6,664,076 B2 | 12/2003 | Green et al. | |
| 7,691,620 B2 | 4/2010 | Green et al. | |
| 8,021,865 B2 | 9/2011 | Atkinson et al. | |
| 8,143,038 B2 | 3/2012 | Atkinson et al. | |
| 2002/0034816 A1 | 3/2002 | Green et al. | |
| 2008/0305536 A1 | 12/2008 | Atkinson et al. | |
| 2009/0042265 A1 | 2/2009 | Atkinson et al. | |
| 2009/0197314 A1 | 8/2009 | Atkinson et al. | |
| 2011/0217760 A1 | 9/2011 | Atkinson et al. | |
| 2011/0318802 A1 | 12/2011 | Atkinson et al. | |

FOREIGN PATENT DOCUMENTS

| | | |
|---|---|---|
| EP | 0124076 A2 | 11/1984 |
| EP | 0351717 A2 | 1/1990 |
| EP | 0937774 A1 | 8/1999 |
| FR | 2 477 572 A | 9/1981 |
| GB | 2 074 188 A | 8/1981 |
| GB | 2171703 A | 9/1986 |
| JP | 2005-261239 A | 9/2005 |
| WO | WO88/09379 A2 | 12/1988 |
| WO | WO 98/45425 A1 | 10/1998 |
| WO | WO 01/49865 A1 | 7/2001 |
| WO | WO 01/83784 A2 | 11/2001 |
| WO | WO 02/29030 A2 | 4/2002 |
| WO | WO 2006/117536 A1 | 11/2006 |
| WO | WO 2006/131734 A1 | 12/2006 |
| WO | WO 2007/039753 A1 | 4/2007 |
| WO | WO 2009/022158 A1 | 2/2009 |
| WO | WO 2010/052499 A1 | 5/2010 |

OTHER PUBLICATIONS

Germain et al. (Appl. Microbiol. Biotechnol., vol. 24, pp. 300-305, 1986).*
Lapierre et al. (Appl. Environ. Microbiol., 65 (9) 1999, 4002-4007).*
de Graef (J. of Bacter., Apr. 1999, vol. 181, No. 8, pp. 2351-2357).*
Witkowski et al., Conversion of a β-Ketoacyl Synthase to a Malonyl Decarboxylase by Replacement of the Active-Site Cysteine with Glutamine. Biochemistry 38:11643-11650, 1999.*
Seffernick et al., Melamine Deaminase and Atrazine Chlorohydrolase: 98 Percent Identical but Functionally Different. J. Bacteriol. 183(8):2405-2410, 2001.*
Underwood et al., Genetic Changes to Optimize Carbon Partitioning between Ethanol and Biosynthesis in Ethanologenic *Escherichia coli*, Applied and Environmental Microbiology, 68:12, p. 6263-6272, 2002.*
Desai et al., Cloning of L-lactate dehydrogenase and elimination of lactic acid production via gene knockout in *Thermoanaerobacterium saccharolyticum* JW/SL-YS485. Appl. Microbiol. Biotechnol. 65: 600-605, 2004.*

(Continued)

*Primary Examiner* — Ganapathirama Raghu
(74) *Attorney, Agent, or Firm* — Saliwanchik, Lloyd & Eisenschenk

(57) ABSTRACT

A thermophilic microorganism is modified to permit the increased production of ethanol, wherein a first modification is the inactivation of the lactate dehydrogenase gene and a second modification upregulates the pyruvate dehydrogenase gene.

16 Claims, 3 Drawing Sheets

(56) References Cited

OTHER PUBLICATIONS

Inui et al., Metabolic Engineering of *Corynebacterium glutamicum* for Fuel Ethanol Production under Oxygen-Deprivation Conditions. J Mol Microbiol Biotechnol. 8:243-254, 2004, hereinafter, Inui.*

Breuer, M. et al. "High-throughput assay of (R)-phenylacetylcarbinol synthesized by pyruvate decarboxylase" *Anal Bioanal Chem*, 2002, pp. 1069-1073, vol. 374.

Carlsson, J. et al. "Pyruvate Dehydrogenase Activity in *Streptococcus mutans*" *Infection and Immunity*, 1985, pp. 674-678, vol. 49, No. 3.

Gao, H. et al. "The E1β and E2 Subunits of the *Bacillus subtilis* Pyruvate Dehydrogenase Complex Are Involved in Regulation of Sporulation" *Journal of Bacteriology*, May 2002, pp. 2780-2788, vol. 184, No. 10.

Hollmann, R. et al. "Pyruvate formation and suppression in recombinant *Bacillus megaterium* cultivation" *Journal of Biotechnology*, 2004, pp. 89-96, vol. 111.

Lessard, I.A.D. et al. "Expression in *Escherichia coli* of Genes Encoding the E1α and E1β Subunits of the Pyruvate Dehydrogenase Complex of *Bacillus stearothermophilis* and Assembly of a Functional E1 Component ($\alpha_1\beta_2$) in Vitro" *The Journal of Biological Chemistry*, 1994, pp. 10378-10383, vol. 269, No. 14.

Neveling, U. et al. "Gene and subunit organization of bacterial pyruvate dehydrogenase complexes" *Biochemica et Biophysica Acta*, 1998, pp. 367-372, vol. 1385.

Niu, X.D. et al. "Cloning and nucleotide sequence of the gene for dihydrolipoamide acetyltransferase from *Saccharomyces cerevisiae*" *Proc. Natl. Acad. Sci. USA*, Oct. 1988, pp. 7546-7550, vol. 85.

Schütz, A. et al. "Crystal structure of thiamindiphosphate-dependent indolepyruvate decarboxylase from *Enterobacter cloacae*, an enzyme involved in the biosynthesis of the plant hormone indole-3-acetic acid" *Eur. J. Biochem.*, 2003, pp. 2312-2321, vol. 270.

Schütz, A. et al. "Studies on structure-function relationships of indolepyruvate decarboxylase from *Enterobacter cloacae*, a key enzyme of the indole acetic acid pathway" *Eur. J. Biochem.*, 2003, pp. 2322-2331, vol. 270.

Siegert, P. et al. "Exchanging the substrate specificities of pyruvate decarboxylase from *Zymomonas mobilis* and benzoylformate decarboxylase from *Pseudomonas putida*" *Protein Engineering, Design & Selection*, 2005, pp. 345-357, vol. 18, No. 7.

Tomar, A. et al. "The effect of acetate pathway mutations on the production of pyruvate in *Escherichia coli*" *Appl Microbiol Biotechnol*, 2003, pp. 76-82, vol. 62.

Wendisch, V.F. et al. "Metabolic engineering of *Escherichia coli* and *Corynebacterium glutamicum* for biotechnological production of organic acids and amino acids" *Current Opinion in Microbiology*, 2006, pp. 268-274, vol. 9.

Witzmann, S. et al. "The pyruvate dehydrogenase complex from the thermophilic organisms: thermal stability and re-association from the enzyme components" *Biochemica et Biophysica Acta*, 1998, pp. 341-352, vol. 1385.

Database WPI Week 200567, *Thomson Scientific*, AN 2005-653380, XP002487167 & JP2005-261239A, Sep. 29, 2005.

"*Geobacillus*" retrieved from the NCBI Database via http://www.ncbi.nlm.nih.gov/Taxonomy/Browser/wwwtax.cgi?id=129337 on Mar. 22, 2012, 10 pages.

"*Geobacillus* Lactate Dehydrogenase in UniProtKB" retrived from the UnitProt Database via http://www.uniprot.org/uniprot/?query=geobacillus++lactate+dehydrogenase&sort=score on Mar. 22, 2012, 2 pages.

"*Geobacillus* spo0A in UniProtKB" retrived from the UnitProt Database via http://www.uniprot.org/uniprot/?query=geobacillus+spo0A&sort=score on Mar. 22, 2012, 3 pages.

Office Action dated Mar. 28, 2012 in U.S. Appl. No. 13/127,927, filed May 13, 2011.

Barstow, D.A. et al. "Cloning, expression and complete nucleotide sequence of the *Bacillus stearothermophilus* L-lactate dehydrogenase gene" *Gene*, 1986, 46:47-55, abstract.

Biswas, I. et al. "High-Efficiency Gene Inactivation and Replacement System for Gram-Positive Bacteria," *Journal of Bacteriology*, Jun. 1, 1993, pp. 175(11):3628-3635, Washington, DC, US, XP000563688.

Desai, S.G. et al. "Cloning of L-lactate dehydrogenase and elimination of lactic acid production via gene knockout in *Thermoanaerobacterium saccharolyticum* JW/SL-YS485," *Applied Microbiology and Biotechnology*, Oct. 2004, 65(5):600-605, XP002393736.

Fong, J.C.N. et al. "Isolation and characterization of two novel ethanol-tolerant facultative-anaerobic thermophilic bacteria strains from waste compost" *Extremophiles*, 2006, 10:363-372.

Fortina, M.G. et al. "Reclassification of *Saccharococcus caldoxylosilyticus* as *Geobacillus caldoxylosilyticus* (Ahmad et al. 2000) comb nov" *International Journal of Systematic and Evolutionary Microbiology*, 2001, 51:2063-2071.

*Geobacillus thermoglucosidasius*. NCBI Databases, pp. 1-3, printed from the internet on Oct. 29, 2010.

Hartley, B.S. et al. (May 1983) "Development and Economics of a Novel Thermophilic Ethanol Fermentation" Presentations from Biotech '83 London, May 4-6, 1983 First World Conference, Biotech, Northwood, Online Conf. LTD, GB, pp. 895-905.

Jimenez, J. et al. "Selection of Ethanol-Tolerant Yeast Hybrids in pH-Regulated Continuous Culture" *Applied and Environmental Microbiology*, Apr. 1988, 54(4):917-922.

Kuisiene, N. et al. "Phylogenetic, Inter, and Intraspecific Sequence Analysis of spo0A Gene of the Genus *Geobacillus*" *Curr Microbiol*, 2009, 58:547-553.

Larsen, L. et al. "*Thermoanaerobacter mathranii* sp. Nov., an ethanol-producing, extremely thermophilic anaerobic bacterium from a hot spring in Iceland" *Arch Microbiol*, 1997, 168:114-119.

Lee, D.H. et al. "Ethanol Fermentation of Corn Starch by a Recombinant *Saccharomyces cerevisiae* Having Glucoamylase and α-Amylase Activities" *J. Food Sci. Nutr.*, 2001, 6(4):206-210.

Lewis, R.J. et al. "Domain Swapping in the Sporulation Response Regulator Spo0A" *J. Mol. Biol.*, Mar. 31, 2000, 297(3):757-770.

Lynd, L.R. et al. "Thermophilic Ethanol Production: Investigation of Ethanol Yield and Tolerance in Continuous Culture" *Applied Biochemistry and Biotechnology*, 1991, 28/29:549-570.

Molle, V. et al. "The Spo0A regulon of *Bacillus subtilis*" *Molecular Microbiology*, 2003, 50(5):1683-1701.

Nakajima, R. et al. "Nucleotide Sequence of the *Bacillus stearothermophilus* α-Amylase Gene" *J. Bacteriol.*, Jul. 1985, 163(1):401-406.

Nichols, N.N. et al. "Engineering lactic acid bacteria with pyruvate decarboxylase and alcohol dehydrogenase genes for ethanol production from *Zymomonas mobilis*" *J Ind Microbiol Biotechnol*, 2003, 30:315-321.

Payton, M.A. "Production of ethanol by thermophilic bacteria," *Trends in Biotechnology*, 1984, 2(6):153-158, Elsevier, Amsterdam, NL, XP000999007.

Rowe-Magnus, D.A. et al. "Identification of a Second Region of the Spo0A Response Regulator of *Bacillus subtilis* Required for Transcription Activation" *J. Bacteriol.*, Aug. 2000, 182(15):4352-4355.

San Martin, R. et al. "Development of a synthetic medium for continuous anaerobic growth and ethanol production with a lactate dehydrogenase mutant of *Bacillus stearothermophilus*," *Journal of General Microbiology*, Feb. 3, 1992, 138:987-996, Great Britain.

San Martin, R. et al. "Pathways of ethanol production from sucrose by a mutant thermophilic *Bacillus* in continuous culture," *Journal of General Microbiology*, Jan. 5, 1993, 139:1033-1040, Great Britain.

Stephenson, K. et al. "Molecular insights into the initiation of sporulation in Gram-positive bacteria: new technologies for an old phenomenon" *FEMS Microbiology Reviews*, 2005, 29:281-301.

Yomano, L.P. et al. "Isolation and characterization of ethanol-tolerant mutants of *Escherichia coli* KO11 for fuel ethanol production" *Journal of Industrial Microbiology & Biotechnology*, Feb. 1998, 20(2):132-138.

Office Action dated May 5, 2010 in U.S. Appl. No. 11/915,930, filed Sep. 29, 2008.

Office Action dated Nov. 15, 2010 in U.S. Appl. No. 11/915,930, filed Sep. 29, 2008.

Office Action dated Nov. 17, 2009 in U.S. Appl. No. 11/913,480, filed Apr. 17, 2008.

(56) References Cited

OTHER PUBLICATIONS

Office Action dated Jun. 25, 2010 in U.S. Appl. No. 11/913,480, filed Apr. 17, 2008.
Office Action dated Jun. 16, 2011 in U.S. Appl. No. 12/066,526, filed Jun. 29, 2008.
Office Action dated Feb. 18, 2011 in U.S. Appl. No. 12/066,526, filed Jun. 29, 2008.
Office Action dated Sep. 15, 2011 in U.S. Appl. No. 13/127,927, filed May 13, 2011.
Office Action dated Oct. 14, 2011 in U.S. Appl. No. 13/191,056, filed Jul. 26, 2011.

* cited by examiner

```
                         SEQUENCE LISTING

<160> NUMBER OF SEQ ID NOS: 32

<210> SEQ ID NO 1
<211> LENGTH: 29
<212> TYPE: DNA
<213> ORGANISM: Artificial
<220> FEATURE:
<223> OTHER INFORMATION: Primer sequence

<400> SEQUENCE: 1
ggaattccct tatgaaccaa ggaatagca                                         29

<210> SEQ ID NO 2
<211> LENGTH: 31
<212> TYPE: DNA
<213> ORGANISM: Artificial
<220> FEATURE:
<223> OTHER INFORMATION: Primer sequence

<400> SEQUENCE: 2
gcggccgcac ccgctctttc ggtaacccgc t                                      31

<210> SEQ ID NO 3
<211> LENGTH: 31
<212> TYPE: DNA
<213> ORGANISM: Artificial
<220> FEATURE:
<223> OTHER INFORMATION: Primer sequence

<400> SEQUENCE: 3
gcggccgctt gctaagtgaa tattttcaag t                                      31

<210> SEQ ID NO 4
<211> LENGTH: 28
<212> TYPE: DNA
<213> ORGANISM: Artificial
<220> FEATURE:
<223> OTHER INFORMATION: Primer sequence

<400> SEQUENCE: 4
ctgcagcgtc aattccatca cttcacga                                          28

<210> SEQ ID NO 5
<211> LENGTH: 25
<212> TYPE: DNA
<213> ORGANISM: Artificial
<220> FEATURE:
```

```
<223> OTHER INFORMATION: Primer sequence

<400> SEQUENCE: 5
acaagcaaaa gaagatatta aagag                                              25

<210> SEQ ID NO 6
<211> LENGTH: 25
<212> TYPE: DNA
<213> ORGANISM: Artificial
<220> FEATURE:
<223> OTHER INFORMATION: Primer sequence

<400> SEQUENCE: 6
tttaagtgct ctaggaaaat aacag                                              25

<210> SEQ ID NO 7
<211> LENGTH: 34
<212> TYPE: DNA
<213> ORGANISM: Artificial
<220> FEATURE:
<223> OTHER INFORMATION: Primer sequence

<400> SEQUENCE: 7
aatctagaca tatgggtgcg aaaacatcca gatt                                    34

<210> SEQ ID NO 8
<211> LENGTH: 31
<212> TYPE: DNA
<213> ORGANISM: Artificial
<220> FEATURE:
<223> OTHER INFORMATION: Primer sequence

<400> SEQUENCE: 8
ccaagctttc tttaatatct tcttttgctt g                                       31

<210> SEQ ID NO 9
<211> LENGTH: 31
<212> TYPE: DNA
<213> ORGANISM: Geobacillus thermoglucosidasius

<400> SEQUENCE: 9
ccggtaccaa agagggcaat ctgaaaggaa g                                       31

<210> SEQ ID NO 10
<211> LENGTH: 28
<212> TYPE: DNA
<213> ORGANISM: Geobacillus thermoglucosidasius

<400> SEQUENCE: 10
ggcatatgtg tctgtcatcc tttccaaa                                           28

<210> SEQ ID NO 11
<211> LENGTH: 30
<212> TYPE: DNA
<213> ORGANISM: Geobacillus thermoglucosidasius

<400> SEQUENCE: 11
ccggtacctg atgtaattgg atgtgatgat                                         30

<210> SEQ ID NO 12
<211> LENGTH: 28
<212> TYPE: DNA
<213> ORGANISM: Geobacillus thermoglucosidasius

<400> SEQUENCE: 12
```
ggcatatgtg tctgtcatcc tttccaaa                                        28

<210> SEQ ID NO 13
<211> LENGTH: 31
<212> TYPE: DNA
<213> ORGANISM: Geobacillus stearothermophilus

<400> SEQUENCE: 13
ccggtaccgc gggacggggg a gctgagtgct c                                  31

<210> SEQ ID NO 14
<211> LENGTH: 31
<212> TYPE: DNA
<213> ORGANISM: Geobacillus stearothermophilus

<400> SEQUENCE: 14
ggcatatgat tcatcctccc tcaatataat g                                    31

<210> SEQ ID NO 15
<211> LENGTH: 30
<212> TYPE: DNA
<213> ORGANISM: Geobacillus stearothermophilus

<400> SEQUENCE: 15
ccggtaccgc gggacgggga gctaggcgcc                                      30

<210> SEQ ID NO 16
<211> LENGTH: 30
<212> TYPE: DNA
<213> ORGANISM: Geobacillus stearothermophilus

<400> SEQUENCE: 16
ggcatatgta ttcacctctt cttccttttt                                      30

<210> SEQ ID NO 17
<211> LENGTH: 31
<212> TYPE: DNA
<213> ORGANISM: Geobacillus stearothermophilus

<400> SEQUENCE: 17
ccggtaccga tcatcccccg ctcccttctc c                                    31

<210> SEQ ID NO 18
<211> LENGTH: 30
<212> TYPE: DNA
<213> ORGANISM: Geobacillus stearothermophilus

<400> SEQUENCE: 18
aacatatggc ccttcccccct taatcaaatg                                     30

<210> SEQ ID NO 19
<211> LENGTH: 30
<212> TYPE: DNA
<213> ORGANISM: Geobacillus stearothermophilus

<400> SEQUENCE: 19
ccggtaccta tgtgtaaaaa tacaagagag                                      30

<210> SEQ ID NO 20
<211> LENGTH: 30
<212> TYPE: DNA
<213> ORGANISM: Geobacillus stearothermophilus

```
<400> SEQUENCE: 20
ggcatatgaa tcgaacctcc ccaagtttat                              30

<210> SEQ ID NO 21
<211> LENGTH: 48
<212> TYPE: DNA
<213> ORGANISM: Geobacillus stearothermophilus

<400> SEQUENCE: 21
ccggtaccta tgataacaaa actaaataag atggatatgt gtaaaaat          48

<210> SEQ ID NO 22
<211> LENGTH: 30
<212> TYPE: DNA
<213> ORGANISM: Geobacillus stearothermophilus

<400> SEQUENCE: 22
ggcatatgaa tcgaacctcc ccaagtttat                              30

<210> SEQ ID NO 23
<211> LENGTH: 30
<212> TYPE: DNA
<213> ORGANISM: Bacillus cereus

<400> SEQUENCE: 23
ccggtaccag ttaacactat atatatagta                              30

<210> SEQ ID NO 24
<211> LENGTH: 30
<212> TYPE: DNA
<213> ORGANISM: Bacillus cereus

<400> SEQUENCE: 24
ggcatatgaa tctcctccat ttttgattag                              30

<210> SEQ ID NO 25
<211> LENGTH: 33
<212> TYPE: DNA
<213> ORGANISM: Artificial
<220> FEATURE:
<223> OTHER INFORMATION: Primer sequence

<400> SEQUENCE: 25
cgtgaaaacg gwggcgtyct tgatatggat aca                          33

<210> SEQ ID NO 26
<211> LENGTH: 26
<212> TYPE: DNA
<213> ORGANISM: Artificial
<220> FEATURE:
<223> OTHER INFORMATION: Primer sequence

<400> SEQUENCE: 26
ttcgcacctg gwgcaaaygg ttctcc                                  26

<210> SEQ ID NO 27
<211> LENGTH: 30
<212> TYPE: DNA
<213> ORGANISM: Artificial
<220> FEATURE:
<223> OTHER INFORMATION: Primer sequence

<400> SEQUENCE: 27
ccggaatttc acttcccacg gaccaggtta                              30
```

```
<210> SEQ ID NO 28
<211> LENGTH: 31
<212> TYPE: DNA
<213> ORGANISM: Artificial
<220> FEATURE:
<223> OTHER INFORMATION: Primer sequence

<400> SEQUENCE: 28
aagcggccgc tatccaagaa ggtggaaacg c                              31

<210> SEQ ID NO 29
<211> LENGTH: 32
<212> TYPE: DNA
<213> ORGANISM: Artificial
<220> FEATURE:
<223> OTHER INFORMATION: Primer sequence

<400> SEQUENCE: 29
aagcggccgc tgcgcgtcga atttggcgat ga                             32

<210> SEQ ID NO 30
<211> LENGTH: 30
<212> TYPE: DNA
<213> ORGANISM: Artificial
<220> FEATURE:
<223> OTHER INFORMATION: Primer sequence

<400> SEQUENCE: 30
ccaagcttcc gtatacaacg ttagacgtaa                                30

<210> SEQ ID NO 31
<211> LENGTH: 27
<212> TYPE: DNA
<213> ORGANISM: Artificial
<220> FEATURE:
<223> OTHER INFORMATION: Primer sequence

<400> SEQUENCE: 31
aygcccgttt aaatgrtcga tttcatg                                   27

<210> SEQ ID NO 32
<211> LENGTH: 23
<212> TYPE: DNA
<213> ORGANISM: Artificial
<220> FEATURE:
<223> OTHER INFORMATION: Primer sequence

<400> SEQUENCE: 32
cgaagtggct ggcaatttgg ctt                                       23
```

THERMOPHILIC MICROORGANISMS FOR ETHANOL PRODUCTION

CROSS-REFERENCE TO RELATED APPLICATION

This application is the National Stage of International Application Number PCT/GB2007/003699, filed Sep. 28, 2007, which is hereby incorporated by reference herein in its entirety, including any figures, tables, nucleic acid sequences, amino acid sequences, or drawings.

FIELD OF THE INVENTION

This invention relates to the production of ethanol as a product of bacterial fermentation. In particular, the invention relates to ethanol production by thermophilic bacteria.

BACKGROUND TO THE INVENTION

Bacterial metabolism can occur through various different mechanisms depending on the bacterial species and environmental conditions. Hetrotrophic bacteria, which include all pathogens, obtain energy from oxidation of organic compounds, with carbohydrates (particularly glucose), lipids and protein being the most commonly oxidised compounds. Biologic oxidation of these organic compounds by bacteria results in synthesis of ATP as the chemical energy source. The process also permits generation of more simple organic compounds (precursor molecules) which are required by the bacterial cell for biosynthetic reactions. The general process by which bacteria metabolise suitable substrates is glycolysis, which is a sequence of reactions that converts glucose into pyruvate with the generation of ATP. The fate of pyruvate in the generation of metabolic energy varies depending on the microorganism and the environmental conditions. There are three principal reactions of pyruvate.

First, under aerobic conditions, many micro-organisms will generate energy using the citric acid cycle and the conversion of pyruvate into acetyl coenzyme A, catalysed by pyruvate dehydrogenase (PDH).

Second, under anaerobic conditions, certain ethanologenic organisms can carry out alcoholic fermentation by the decarboxylation of pyruvate into acetaldehyde, catalysed by pyruvate decarboxylase (PDC) and the subsequent reduction of acetaldehyde into ethanol by NADH, catalysed by alcohol dehydrogenase (ADH).

A third process is the conversion of pyruvate into lactate which occurs through catalysis by lactate dehydrogenase (LDH).

There has been much interest in using micro-organisms for the production of ethanol using either micro-organisms that undergo anaerobic fermentation naturally or through the use of recombinant micro-organisms which incorporate the pyruvate decarboxylase and alcohol dehydrogenase genes. Although there has been some success in producing ethanol by using these micro-organisms, fermentation is often compromised by the increased concentration of the ethanol, especially where the micro-organism has a low level of ethanol tolerance.

Thermophilic bacteria have been proposed for ethanol production, and their use has the advantage that fermentation can be carried out at elevated temperatures which allows the ethanol produced to be removed as vapour at temperatures above 50° C.; this also permits fermentation to be carried out using high sugar concentrations. However, finding suitable thermophilic bacteria which can produce ethanol efficiently is problematic.

WO88/09309 discloses the production of ethanol using thermophilic Bacillus strain LLD-R. LLD-R is a sporulation-deficient strain that arose spontaneously from culture, and in which the ldh gene has been inactivated by spontaneous mutation or by chemical mutagenesis. The strain is however unstable, as indicated below.

WO01/49865 discloses a Gram-positive bacterium which has been transformed with a heterologous gene encoding pyruvate decarboxylase and which has native alcohol dehydrogenase function, for the production of ethanol. The bacterium is a thermophilic Bacillus and the bacterium may be modified by the inactivation of the lactate dehydrogenase gene using transposon insertion. The bacteria disclosed in WO01/49865 are all derived from Bacillus Strain LLD-R. Strains LN and TN are disclosed as improved derivatives of strain LLD-R. However, all strains contain a Hae III type restriction systems that impedes plasmid transformation and therefore prevents the transformation within un-methylated DNA.

WO01/85966 discloses microorganisms that are prepared by in vivo methylation to overcome the restriction problems. This requires transformation with Hae III methyltransferase from Haemophilus aegyptius into strains LLD-R, LN and TN. However, strains LLD-R, LN and TN are unstable mutants and spontaneously revert to lactate-producing wild-type strains, particularly at low pH and in high sugar concentrations. This results in fermentation product changes from ethanol to lactate, making the strains unsuitable for ethanol production.

WO02/29030 discloses that strain LLD-R and its derivatives include a naturally-occurring insertion element (IE) in the coding region of the ldh gene. Transposition of this into (and out of) the ldh gene and subsequent gene inactivation is unstable, resulting in reversion. The proposed solution to this was to integrate plasmid DNA into the IE sequence.

Therefore, in the art, the production of microorganisms for ethanol production relies on modifying laboratory-produced chemically mutated Bacillus microorganisms, treating these with in vivo methylation procedures and further modifying the microorganisms to integrate plasmid DNA into the IE sequence. The procedure is complex, uncertain and there are also regulatory issues on how the strains can be used.

There is therefore a need for improved microorganisms for ethanol production.

SUMMARY OF THE INVENTION

According to a first aspect of the present invention, a thermophilic microorganism is modified to permit the increased production of ethanol, wherein a first modification is the inactivation of the lactate dehydrogenase gene and a second modification upregulates the pyruvate dehydrogenase gene.

The microorganism of the invention shows increased ethanol production compared to wild-type.

According to a second aspect of the present invention, a method for the production of ethanol comprises culturing a microorganism according to the definition provided above under suitable conditions in the presence of a $C_3$, $C_5$ or $C_6$ sugar.

DESCRIPTION OF THE DRAWINGS

The present invention is described with reference to the accompanying figures, wherein.

DESCRIPTION OF THE INVENTION

Figure 1:
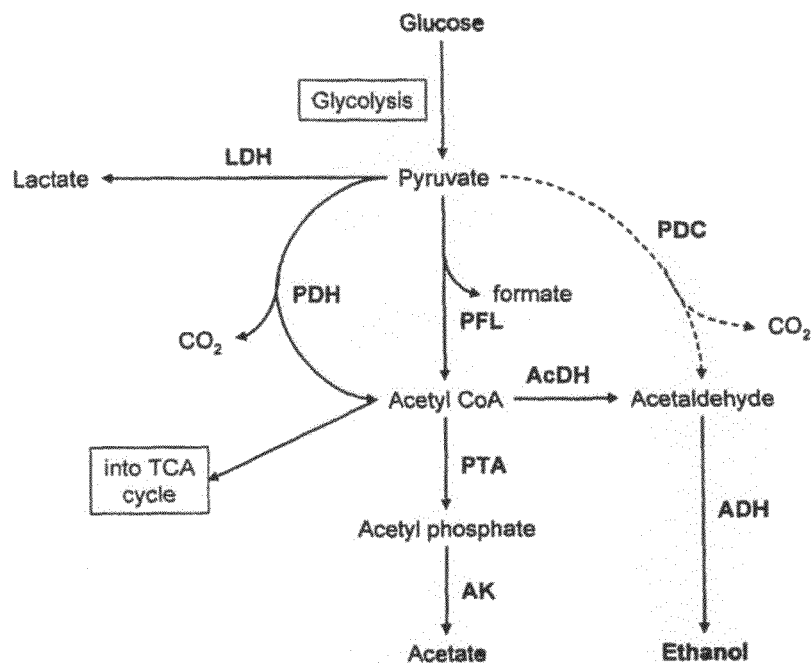
FIG. 1 illustrates schematically the metabolic pathway of glycolysis.

The present invention is based on the modification of a thermophilic microorganism to disrupt the expression of the lactate dehydrogenase gene and to upregulate the PDH gene.

Inactivating the lactate dehydrogenase gene helps to prevent the breakdown of pyruvate into lactate, and therefore promotes (under appropriate conditions) the breakdown of pyruvate into ethanol using pyruvate decarboxylase and alcohol dehydrogenase. It is preferred if the lactate dehydrogenase gene is disrupted by a deletion within or of the gene.

Upregulating the PDH gene promotes the conversion of pyruvate into acetyl CoA, which can then be used, under appropriate conditions, to produce acetaldehyde and eventually ethanol using acetaldehyde dehydrogenase. A further advantage of upregulating PDH is that pyruvate levels, which have an inhibitory effect on glucose uptake and glycolysis, are reduced. This further promotes ethanol production.

The microorganism may be any thermophilic microorganism, but it is preferred if the microorganism is of the *Bacillus* spp. In particular, it is preferred if the microorganism is a wild-type microorganism of the *Geobacillus* species, in particular *Geobacillus thermoglucosidasius*.

In a preferred embodiment, the microorganisms selected for modification are said to be "wild-type", i.e. they are not laboratory-produced mutants. The microorganisms may be isolated from environmental samples expected to contain thermophiles. Isolated wild-type microorganisms will have the ability to produce ethanol but, unmodified, lactate is likely to be the major fermentation product. The isolates are also selected for their ability to grow on hexose and/or pentose sugars, and oligomers thereof, at thermophilic temperatures.

It is preferable that the microorganism of the invention has certain desirable characteristics which permit the microorganism to be used in a fermentation process.

The microorganism should preferably have no restriction system, thereby avoiding the need for in vivo methylation. In addition, the microorganism should be stable to at least 3% ethanol and should have the ability to utilise $C_3$, $C_5$ and $C_6$ sugars (or their oligomers) as a substrate, including cellobiose and starch. It is preferable if the microorganism is transformable at a high frequency. Furthermore, the microorganism should have a growth rate in continuous culture to support dilution rates of 0.3 $h^{-1}$ and above (typically 0.3 $OD_{600}$).

The microorganism will be a thermophile and will grow in the temperature range of 40° C.-85° C. Preferably, the microorganism will grow within the temperature range 50° C.-70° C. In addition, it is desirable that the microorganism grows in conditions of pH7.2 or below, in particular pH6.9-pH4.5.

The microorganism may be a spore-former or may not sporulate. The success of the fermentation process does not depend necessarily on the ability of the microorganism to sporulate, although in certain circumstances it may be preferable to have a sporulator, when it is desirable to use the microorganisms as an animal feedstock at the end of the fermentation process. This is due to the ability of sporulators to provide a good immune stimulation when used as an animal feed-stock. Spore-forming microorganisms also have the ability to settle out during fermentation, and therefore can be isolated without the need for centrifugation. Accordingly, the microorganisms can be used in an animal feed-stock without the need for complicated or expensive separation procedures.

The nucleic acid sequence for lactate dehydrogenase is now known. Using this sequence, it is possible for the skilled person to target the lactate dehydrogenase gene to achieve inactivation of the gene through different mechanisms. It is preferred if the lactate dehydrogenase gene is inactivated either by the insertion of a transposon, or, preferably, by the deletion of the gene sequence or a portion of the gene sequence. Deletion is preferred, as this avoids the difficulty of reactivation of the gene sequence which is often experienced when transposon inactivation is used. In a preferred embodiment, the lactate dehydrogenase gene is inactivated by the integration of a temperature-sensitive plasmid (plasmid pUB190-ldh as disclosed in PCT/GB06/01586), which achieves natural homologous recombination or integration between the plasmid and the microorganism's chromosome. Chromosomal integrants can be selected for on the basis of their resistance to an antibacterial agent (for example, kanamycin). The integration into the lactate dehydrogenase gene may occur by a single cross-over recombination event or by a double (or more) cross-over recombination event. It is preferred that a double cross-over event is carried out, to remove the LDH gene (or part thereof) and the initial integrant, ie. the temperature-sensitive plasmid. In this way, the mutant microorganisms will not contain any heterologous DNA and will not therefore be classified as a genetically-modified organism (GMO) according to the GMO regulations.

The second modification is to upregulate PDH. PDH is a large enzyme complex, containing three units—E1: pyruvate decarboxylase (EC 1.2.4.1, not EC 4.1.1.1), E2: dihydrolipoamide transacetylase, and E3: dihydrolipoamide dehydrogenase. The complex requires several cofactors which includes NAD, FAD, coenzyme A lipoic acid and thiamine pyrophosphate (TPP). Four genes code for the complex as the E1 unit is a heterodimer of α and β subunits and are often described as pdhA, pdhB, pdhC and pdhD (E1α, E1β, E2 and E3 respectively). The E1 unit of PDH requires TPP in the same way that PDC EC 4.1.1.1 requires TPP and catalyses a similar decarboxylation reaction, but in the presence of coenzyme A and lipoic acid—carried by other enzyme units—the product is acetyl CoA rather than acetaldehyde. However, PDC activity of the E1 unit has been measured when it has not been complexed with other units in PDH (Lessard & Perham; *The Journal of Biological Chemistry;* 1994, 269:14, 10378-10383; Tomar et al; *Applied Microbiology and Biotechnology;* 2003, 62, 76-82; Frank et al; *Science;* 2004, 306: October 29, 872-876, supplementary data). Accordingly, PDC activity of EC 1.2.4.1 may be enhanced by the upregulation of PDH so that acetaldehyde is produced over and above acetyl CoA. Enhanced PDH activity is also being sought to remove the pyruvate bottleneck to allow more ethanol to be produced with less acetate and formate as side products.

To this end, the PDH genes and surrounding sequence was isolated using standard "genome walking" techniques. Approximately 8.8 kb of DNA was isolated, sequenced and found to contain the following genes shown in FIG. 2 and Table 1.

TABLE 1

| Gene | Position (bp) | Proposed function | Frame (aa's at 5' and 3') | Size (aa) |
|---|---|---|---|---|
| pdf2 | 746-192 | Peptide deformylase | −3 (MIT-IER) | 184 |
| orf2 | 868-1497 | Unknown - Hypothetical protein | +1 (MQR-IWK) | 209 |
| pdhA(α) | 1875-2984 | α - subunit of pyruvate hydrogenase | +3 (MGA-ESK) | 369 |
| pdhA(β) | 3003-3965 | β - subunit of pyruvate dehydrogenase | +3 (MIQ-INF) | 320 |
| pdhB | 4058-5368 | Dihydrolipoamide transacetylase | +2 (VAF-MEA) | 436 |
| lpd | 5373-6785 | Lipoamide dehydrogenase | +3 (MVV-ISK) | 470 |
| orf7 | 7432-6833 | Unknown - Hypothetical protein | −1 (MNK-CTE) | 199 |
| orf8 | 7964-8647 | Transposase | +2 (MDL-SPP) | 227 |

Figure 2:
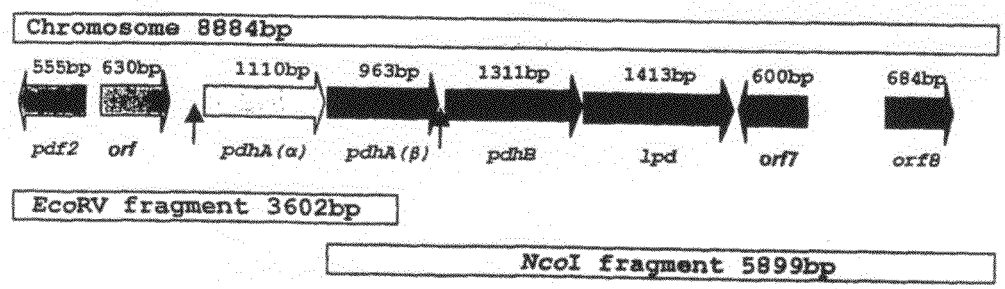
FIG. 2 illustrates the genes of the PDH complex.

The hypothetical promoter regions are shown in FIG. 2 (arrows)—one upstream from the start of pdhA and possible second promoter ahead of pdhC. A previous example of a secondary promoter in the PDH cluster was reported for *Bacillus subtilis* (Gao et al; *Journal of Bacteriology*, 2002, 184:10, 2780-2788), but most described PDH gene clusters have just one promoter upstream of the cluster (Neveling at al; *Biochimica Acta;* 1998 1385, 367-372. The upregulation can be carried out using techniques known in the art. In particular, upregulation can be carried out by introducing a suitable promoter or enhancer sequence upstream of the PDH complex.

The enzyme complex is known to work under both aerobic and anaerobic conditions (Carlsson at al; *Infection and Immunity;* 1985, 49:3, 674-678) but it is generally considered to be an aerobic enzyme (Ch 15; *Principles of Biochemistry*; Lehninger, Nelson & Cox; $2^{nd}$ Ed, Worth Publishers, New York, 1993, p 447) with pyruvate formate lyase (PFL) its anaerobic counterpart. Both enzymes convert pyruvate, formed in glycolysis, to acetyl CoA to feed into the TCA cycle but the cycle only works completely under aerobic conditions. However, as it is desirable to use anaerobic conditions, promoters that operate in anaerobic conditions are preferred for use in the invention. Thus promoters for enzymes believed to work under anaerobic conditions—examples being the LDH promoters (P ldh from *G. stearothermophilius* NCA1503, DSM13240 and ATCC14579) and ferredoxin promoters (P ferrA from *G. stearothermophilius* DSM13240)—were identified, isolated and stably integrated in the appropriate site, just upstream from the start of pdhA. The strains used and the promoters inserted into the PDH complex are shown in Table 2. In most examples the promoters produce a ten-fold increase in PDH expression, increase in glucose consumption, reducing pyruvate to negligible levels and a ~50% increase in ethanol production. Interestingly acetate levels remained the same resulting in an increase in the ethanol: acetate ratio in favour of ethanol production.

TABLE 2

| Strain | Promoter | mM Glucose | mM Ethanol | mM Pyruvate | mM Acetate |
|---|---|---|---|---|---|
| TM177 | P ldh(1503) | 0.0 | 159.4 | 0.0 | 18.8 |
| TM178 | P ldh(1503) | 0.0 | 164.0 | 0.0 | 21.1 |
| TM216 | P ldh(1503) dimer | 0.0 | 163.4 | 0.0 | 19.6 |
| TM218 | P ldh(1503) dimer | 0.0 | 152.1 | 0.0 | 21.0 |
| TM226 | P ldh(13240) | 0.0 | 155.8 | 0.0 | 20.9 |
| TM227 | P ldh(13240) | 0.0 | 158.4 | 0.0 | 19.4 |
| TM228 | P pfl1 | 0.0 | 152.1 | 0.0 | 22.3 |
| TM229 | P pfl1 | 0.0 | 146.0 | 0.0 | 19.9 |
| TM230 | P pfl2 | 0.0 | 150.6 | 0.0 | 17.8 |
| TM231 | P pfl2 | 0.0 | 148.6 | 0.0 | 19.5 |
| TM180 | P ldh(1503) DCO | 0.0 | 152.0 | 0.0 | 21.7 |
| TM89 | (control) | 23.2 | 92.7 | 12.2 | 21.9 |

In a preferred embodiment, a third modification is introduced to enhance the PDC activity. This can be carried out by inactivating E2 (EC2.3.1.12). Inactivation can be carried out in a manner similar to the inactivation of LDH, but with the E2 gene as the target for disruption.

In a further embodiment, a microorganism of the invention comprises a further modification, inactivating the pyruvate formate lyase gene, thereby preventing/reducing the conversion of pyruvate to acetyl CoA and formate. Pyruvate formate lyase (PFL) is the "anaerobic counterpart" to pyruvate dehydrogenase (PDH) and converts pyruvate to acetyl CoA and formate (see FIG. 1). While acetyl CoA can be converted to ethanol via acetaldehyde dehydrogenase (AcHD), formate is an undesired side product which has the potential to inhibit growth in ethanolgenic organisms.

PFL was chosen as a target for knockout in order to promote the metabolic flux towards ethanol production and to improve the redox balance of the remaining pathway to ethanol synthesis. An additional advantage is the elimination of formate production. PFL activity can be inactivated using the same protocol for the LDH knockout (described below) to produce a mutant which does not rely on antibiotic selection for the continuation of the altered phenotype. In this embodiment, it is preferred that the microorganism comprises both the lactate dehydrogenase inactivation and the upregulation of the pyruvate dehydrogenase, so that, under anaerobic conditions, ethanol production is increased.

The PFL gene can be inactivated using the techniques disclosed for the inactivation of LDH. Transposon insertion may be used, or gene deletion (or partial gene deletion) may be used. It is preferred that gene deletion (or partial deletion) is used.

In a further preferred embodiment, the micro-organism will also comprise a heterologous alcohol dehydrogenase gene. The expression of this heterologous gene results in the production of enzymes which redirect the metabolism so that ethanol is the primary fermentation product. The gene may be obtained from micro-organisms that typically undergo anaerobic fermentation, including *zymomonas* species, including *zymomonas mobilis*.

Methods for the preparation and incorporation of the gene into microorganisms are known, for example in Ingram at al, Biotech & BioEng, 1998; 58 (2+3): 204-214 and U.S. Pat. No. 5,916,787, the content of each being incorporated herein by reference. The gene may be introduced in a plasmid or integrated into the chromosome, as will be appreciated by the skilled person.

The microorganisms of the invention may be cultured under conventional culture conditions, depending on the thermophilic microorganism chosen. The choice of substrates, temperature, pH and other growth conditions can be selected based on known culture requirements, for example see WO01/49865 and WO01/85966, the content of each being incorporated herein by reference.

The present invention will now be described, by way of example only, with reference to the accompanying drawings, in the following examples.

Inactivation of the LDH Gene

Example 1

Generation of a Stable LDH Mutant

A strategy was designed to generate a stable mutation of the LDH gene in *Geobacillus thermoglucodasius* NCIMB 11955 by gene replacement and followed two approaches.

In approach 1, two existing unique restriction sites near the middle of the LDH coding sequence were exploited to generate a deletion. A single large PCR product was generated from genomic DNA covering most of the available LDH sequence, and cloned into the SmaI site in the multiple cloning site of pUC19 (New England Biolabs). The pUC19 clone was then digested sequentially with BstEII and BsrGI and relegated after Klenow digestion, to generate an internal deletion in the LDH gene between BstEII and BsrGI.

In approach 2, the LDH gene was cloned as two PCR products, introducing NotI sites with the oligo primers below, to allow the two PCR products to be ligated together in pUC190, with the generation of a deletion in the middle of the LDH sequence.

The LDH genes resulting from each approach, having the internal deletions, were subcloned into three potential delivery systems: pUB190, pNW33N and TMO19.

Table 3 shows the PCR primers used for deletion approach 2.

|  | Sequence |  | Underlined restriction site |
|---|---|---|---|
| Primer 1 (forward) | GGAATTCCCTTATGAACCAAGGAATAGCA | SEQ ID NO: 1 | EcoRI |
| Primer 2 (reverse) | GCGGCCGCACCCGCTCTTTCGGTAACCCGCT | SEQ ID NO: 2 | NotI |
| Primer 3 (forward) | GCGGCCGCTTGCTAAGTGAATATTTTCAAGT | SEQ ID NO: 3 | NotI |
| Primer 4 (reverse) | CTGCAGCGTCAATTCCATCACTTCACGA | SEQ ID NO: 4 | PstI |

Shaded sequence indicates bases added to complete the restriction site.

Table 4 lists the properties of the delivery vectors.

|  | pUB190 | pNW33N | pTM019 |
|---|---|---|---|
| Selectable Marker | Kanamycin adenyltransferase. Growth and viable count reduced at 60° C. cf 52° C. No growth at 68° C. Generally, tight selection, no satellites, relatively heat stable, but do see spontaneous resistance. | Chloramphenicol acetyl transferase. Growth and viable count slightly reduced at 60° C. cf 52° C. No growth at 65° C. Generally, relatively heat-labile, minor problem with satellites, but very low generation of spontaneous resistance. | pTM019 was derived by insertion of kan PCR product (pUB190 used as template) into the EcoR I site of pNW33N, passed though and re-isolated from *G. thermoglucosidasius*. Thus should have similar selection properties to that of pUB190 and pNW33N |
| Transformability | Good (approx 1,000 in one experiment). | Very good, >2,000 per experiment, reproducible. | Moderate (~400 per experiment). This is probably due to the larger size of the vector |
| Available cloning sites | Limited, part of multiple cloning site lost in construction. | Good - multiple cloning site intact. | Good - multiple cloning site intact. |

Approach 1: Preparation of Genomic DNA

Genomic DNA was prepared from 11955 to serve as a template for PCR. Cells from a 20 mL overnight culture of 11955 (TGP media, 52° C.) were collected by centrifugation (4000 rpm, 20 mins). The cell pellet was resuspended in 5 mL STE buffer (0.3 M sucrose, 25 mM Tris-HCl, 25 mM EDTA, pH 8) containing 2.5 mg lysozyme and 50 μL of ribonuclease A (1 mg/mL). This was incubated for 1 hour at 30° C. before the addition of 5 mg proteinase K and 50 μL 10% SDS followed by a further 1 hour incubation at 37° C. The lysed culture was then extracted sequentially with equal volumes of phenol:chloroform (1:1), followed by chloroform before precipitation with isopropanol. After washing twice with 70% ice-cold ethanol, the DNA pellet was redissolved in 0.5 mL TE buffer.

Approach 2: Generation of LDH Deletion Constructs

PCR was carried out using a Robocycler Gradient 96 (Stratagene) and reaction conditions were as follows: cycle 1—denaturation at 95° C. for 5 min, annealing at 47° C. for 1 min, extension at 72° C. for 2 mins, Cycles 2-30—denaturation at 95° C. for 1 min, annealing at 47° C. for 1 min, extension at 72° C. for 2 mins, and a final incubation at 72° C. for 5 mins. The enzymes used were an equal mixture of Pfu polymerase (Promega) and Taq polymerase (New England Biolabs, NEB). Buffers and dNTPs used were according to manufacturer's instructions (Pfu, Promega). The DNA template used was the 11955 genomic DNA prepared above and the resulting PCR products were purified via agarose gel electrophoresis followed by elution from the gel using a gel extraction kit (QIAquick Gel extraction kit, Qiagen) according to manufacture's instructions. The purified PCR products were ligated into pUC19 (NEB), previously digested with SmaI, with the ligation mixture used to transform *Escherichia coli* JM109 (Stratagene) using standard protocols. Ampicillin-resistant colonies were selected and the contained plasmids were isolated and characterized by restriction analysis.

A plasmid (pTMO02) with fragment 2 inserted into pUC19 (with the novel PstI site introduced at the 3' end of the fragment and NotI site at the 5' end, produced using primers 3 and 4) was digested with NotI and PstI. The resulting fragment (approximately 0.4 kb) was ligated into a pUC19 plasmid (pTMO01) bearing fragment 1 (produced with primer pair 1 and 2) which had also been digested with NotI and PstI. The ligation mixture was used to transform *E. coli* JM109 (Stratagene) using standard protocols. As before ampicillin-resistant colonies were selected and the contained plasmids were isolated and characterized by restriction analysis, to establish the orientation of the inserts.

A plasmid (pTMO03) with the expected restriction pattern for the desired construct was identified and verified by sequencing using M13mp18 reverse and forward primers.

The mutated LDH gene fragment was excised from pTMO03 by digestion with HindIII and EcoRI and purified through agarose gel electrophoresis as before. The fragment was treated with Klenow polymerase (NEB, according to manufacturer's instructions) to generate blunt ends for ligation into pUB190 which had been digested with XbaI and also treated with Klenow polymerase. The ligation mixture was used to transform *E. coli* SCS110 (Stratagene) using standard protocols. As before ampicillin-resistant colonies were selected and the contained plasmids were isolated and characterized by restriction analysis. A plasmid (pTMO14, based on the pUB190 backbone) with the expected restriction pattern for the desired construct was identified and used to transform NCIMB 11955 by electroporation using the protocol described below.

Electroporation Protocol for *Geobacillus thermoglucosidasius* NCIMB 11955

A frozen stock of 11955 was made by growing an overnight culture in TGP medium (shaken at 250 rpm at 55° C., 50 mL volume in 250 ml conical flask, $OD_{600}$~2), adding an equal volume of 20% glycerol, dividing into 1 mL aliquots and storing in cryotubes at −80° C. 1 mL of this stock was used to inoculate 50 mL of pre-warmed TGP in a 250 ml conical flask which was incubated (55° C., 250 rpm) until an $OD_{600}$ of 1.4 was achieved.

The flask was cooled on ice for 10 minutes, then the culture centrifuged for 20 minutes at 4000 rpm at 4° C. in a 50 mL Falcon tube. The pellet was resuspended in 50 mL ice-cold electroporation medium and centrifuged (4,000 rpm, 20 minutes). Three further washes were carried out in this way (1×25 mL and 2×10 mL), before the pellet was resuspended in 1.5 mL ice-cold electroporation medium, divided into 60 μL aliquots, and stored in 0.5 mL eppendorf tubes at −80° C. for future use (or used immediately).

For the electroporation, 1-2 μL of DNA in water was added to 60 μL of electrocompetent cells in an eppendorf tube kept on ice, and gently mixed. This suspension was transferred to a pre-cooled electroporation cuvette (1 mm gap) and electroporated at 2500V, 10 μF capacitance and 600Ω resistance. Immediately after the pulse, 1 mL of pre-warmed TGP was added, mixed, and the suspension transferred to a screw top tube and was incubated at 52° C. for 1 hour in a shaking waterbath. After incubation the suspension was either plated directly (eg 2×0.5 mL) or centrifuged (4,000 rpm, 20 minutes), resuspended in 200 μL-500 μL TGP, and spread on TGP agar, containing the appropriate antibiotic, and grown overnight at 52° C. Antibiotic-resistant transformants were observed after 24 hours.

| Electroporation medium | TGP medium | |
|---|---|---|
| 0.5M sorbitol | Tryptone | 17 g/L |
| 0.5M mannitol | Soy peptone | 3 g/L |
| 10% glycerol | $K_2HPO_4$ | 2.5 g/L |
| | NaCl | 5 g/L |
| | pH to 7.3 | |
| | Additions post-autoclaving; | |
| | Sodium pyruvate | 4 g/l |
| | Glycerol | 4 ml/L |
| | (from fliter-sterilized concentrate) | |

Selection of Single Crossover LDH Negative Primary Integrants

The plasmids (eg pTMO14) used for integration into the organism's genome were temperature sensitive. The pUB190-based knockout vectors are able to replicate within the host at 54° C. but not above 65° C. Thus to grow in the presence of kanamycin at 68° C. the host has to incorporate the plasmid within the genome.

A kanamycin-resistant colony, from the transformation of *G. thermoglucodasius* NCIMB 11955 with pTMO14, was purified by streaking to single colonies on TGP agar containing 12 μg/mL kanamycin. This transformant was used to generate primary integrants in 11955 by forcing homologous recombination with the genomic LDH allele. This was achieved by growing the strain in 50 mL TGP medium overnight in a 250 mL conical flask at 52° C. and 250 rpm, centrifuging the culture (4,000 rpm, 20 mins) resuspending the cells in 1 mL TGP and spreading on TGP agar plates containing 12 μg/mL kanamycin for overnight incubation at 68° C. Under these conditions, pUB190 cannot replicate as an autonomous plasmid. The majority of colonies obtained in this manner, when tested for lactate production, gave an LDH-phenotype, with increased production of ethanol, indicating the generation of LDH mutants by integration at the LDH locus.

Generation of a Gene Replacement LDH Mutant by Double-Crossover

A presumptive primary integrant (TM15) of pTMO14 was identified from the above transformation and used to obtain double recombinants. This was achieved through five successive sub-cultures of TM15 in TGP medium (5 mL in 50 mL falcon tube, 250 rpm, 1% transfer between sub-cultures) without kanamycin, alternating between 8 hours at 54° C. and 16 hours at 52° C. After these five passages the resulting culture was serially diluted and 100 µL samples were spread on TGP plates and grown overnight. Replica-plating of the resultant colonies onto TGP agar containing 12 µg/mL kanamycin was used to identify kanamycin-sensitive colonies. After streaking to single colonies on agar to purify, these kanamycin sensitive derivatives were tested for lactate production, and as expected, proved a mixture of LDH+ and LDH−. One LDH− derivative, TM89, was further characterized by PCR and Southern blots.

Proof of LDH Gene Replacement

Genomic DNA was prepared from TM15 (primary integrant) and TM89 (presumptive double recombinant LDH−), and used as template for PCR using primers 1 and 4, using the conditions used above. Genomic DNA from 11955 was used as control. The PCR products (approx. 0.8 kb bands were obtained from all three templates) were purified as described previously and samples were digested with NotI before being run on a 0.7% agarose electrophoresis gel. The PCR product of 11955 showed no evidence of NotI digestion, as expected, whereas the PCR product of TM89 gave 2 bands of around 0.4 kb, indicating the replacement of the wild-type gene with the mutated allele. NotI digestion of the PCR product of TM15, the primary integrant, gave predominantly the 2 bands seen with TM89, with a trace of the uncut (0.8 kb) band. This can be explained by the result obtained with Southern blotting of the TM15 genomic DNA.

Genomic DNA of 11955, TM15 and TM89 was digested with NotI, PstI and NotI, and HindIII and NotI, and run on an electrophoresis agarose gel. The DNA was transferred onto a positively-charged nylon membrane (Roche) and hybridized with a probe generated by PCR from the 11955 LDH gene using primers 1 and 4 (Table 3) which was DIG-labeled (DIG-labeling kit, Roche, according to manufacturer's instructions). The hybridizing bands were visualized using the detection kit supplied (Roche). The Southern blot showed evidence of a much-amplified band of approximately 7.5 kb in the NotI digest of TM15, with similarly-amplified bands of approximately 7.0 and 0.4 kb in the HindIII/NotI and PstI/NotI digests of TM15, indicating integration of multiple tandem copies of pTMO14 integrated at the LDH locus in this primary integrant. With all three restriction digests, TM89 showed evidence of a different restriction pattern showing an extra hybridizing band compared to 11955, consistent with gene replacement.

Example 2

Generation of a Stable Up-Regulated PDH Mutant a) Cloning and Sequencing the pdh Cluster Primers 5'-AYGCCCGTTTAAATGRTCGATTTCATG-3' (forward; SEQ ID NO:31) and 5'-CGAAGTGGCTG-GCAATTTGGCTT-3 (reverse; SEQ ID NO:32), were designed based on sequence homology between known *Bacillus* and *Geobacillus* PDH sequences, and were used to amplify a 1.8 kb fragment using genomic DNA from *G. thermoglucosidasius* 11955 as a template. The PCR was carried out as described previously with the purified PCR products ligated into pUC19 (NEB). The ligation mixture was used to transform *E. coli* JM109 (Stratagene) using standard protocols. Ampicillin-resistant colonies were selected and the contained plasmids were isolated, characterized by restriction analysis and sequenced. This first fragment was then used as a probe to screen the following libraries.

Genomic DNA from *G. thermoglucosidasius* 11955 was digested with 10 different restriction enzymes using standard protocols. The restriction enzymes BglII, EcoRV, HindIII and MfeI generated DNA fragments of between 2.5-5 kb in size, which were cloned to form several libraries of colonies (pLITMUS28, New England Biolabs), according to manufacturer's instructions). These libraries were screened with the labeled DNA probe (DIG-labeling kit, Roche, according to manufacturer's instructions).

DNA fragments in any colonies that hybridised with the probe were isolated and sequenced. One clone was identified that contained a 3.6 kb EcoRV genomic DNA fragment spanning the 1.8 kb pdh region previously identified and extending downstream from this region by a further ~1.8 kb. The fragment encoded three complete genes beginning at the 5' region with the peptide deformylase 2 (pdf2). Positioned downstream of pdf2 lies an open reading frame encoding a hypothetical gene (which shows homology to the theoretical protein ykaA (BSU14570) from *B. subtilis*), while downstream the next open reading frame is 1110 bp in size and is believed to encode the pyruvate dehydrogenase A α sub-unit (pdhA (α)). Immediately adjacent to the pdhA(α) gene and extending beyond the 3' end of the EcoRV fragment is a portion of a gene believed to encode the pdhA β sub-unit (pdhA(β)). The tandem arrangement of the pdhA a and β genes conforms to the known pdh gene clusters identified in closely related species.

The approach employed to identify this EcoRV fragment was repeated in order to isolate further DNA sequence. Using forward primer 5'-ACAAGCAAAAGAAGATATTAAA-GAG-3' (SEQ ID NO:5) and reverse primer 5'-TTTAAGT-GCTCTAGGAAAATAACAG-3' (SEQ ID NO:6) that bind at the 3' region of the EcoRV fragment, a new probe, GT-DIG2, was generated by PCR, as before. A range of restriction enzymes, some of which were shown to cut just upstream of the GTDIG-2 region, were used to digest genomic DNA isolated from *G. thermoglucosidasius*.

Fragments derived from NcoI digestion were isolated and cloned as before (pLITMUS28, New England Biolabs, according to manufacturer's instructions). On screening with the GT-DIG2 probe, a clone containing an NcoI DNA fragment consisting of ~6 kb DNA positioned downstream of the EcoRV fragment was identified. The sequences of the NcoI and EcoRV fragments formed one continuous sequence (contig) of 8884 bp in length. Sequence analysis has revealed that this contig houses the pdh gene cluster consisting of four adjacent genes flanked by two putative genes either side. The organisation of the genes encoded within the contig is shown in FIG. 2.

b) Single Crossover PDH Mutants—Proof of Concept

Figure 3:
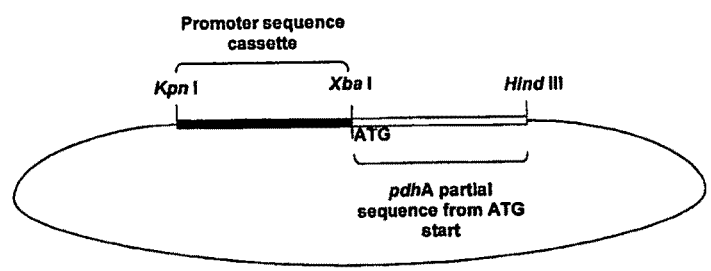
FIG. 3 is a schematic representation of a promoter replacement construct for targeted upregulation of PDH.

The strategy used to generate up-regulated mutants of PDH in LDH− mutants of *G. thermoglucosidasius* 11955 involved the use of the previously identified pdhA sequence to design and generate a cassette with the pdhA coding sequence preceded by a restriction site allowing easy insertion of heterologous promoters, and subsequently inserting them into a suitable integration vector. The requirement was for a strong constitutive promoter such as the LDH-promoter from *G. thermoglucosidasius* or *G. steareothermophilus*. The approach is illustrated in FIG. 3.

The required mutants were generated by transformation of the integration vector into the host strain and selecting for kanamycin-resistant integrants. Such single cross-over mutants are unstable in the absence of antibiotic as the integration event is easily reversible.

i) Development of Vectors for Up-Regulation Work

For the above strategy to work new delivery vectors had to be constructed to allow the use of NdeI restriction sites within the multiple cloning site. The following Table 3 describes and compares the vectors developed with pUB190:

TABLE 5

Vectors constructed for up-regulation work

| | Size(Kb) | Markers | mcs | NdeI | Origin |
|---|---|---|---|---|---|
| pUB190 | 6.7 | amp, kan | No | 3 | pUB110 ligated with pUC19 |
| pTMO19 | 5.4 | cat, kan | Yes | 0 | Kan$^R$ gene from pUB190 inserted into EcoRI site of pNW33N |
| pTMO23 | 2.7 | amp | Yes | 0 | pUC19 with NdeI site removed |
| pTMO31 | 5.1 | amp, kan | Yes | 0 | EcoRI/SnaBI pUB110 fragment inserted into pUC19 | ii) pdhA Backbone Fragment

The pdhA sequence obtained from the original 1.8 kb PCR product cloned into pUC19, described previously, was used to design the forward primer 5'-AATCTAGACATATGGGTGC-GAAAACATCCAGATT-3' (SEQ ID NO:7) incorporating XbaI/NdeI sites, so that the terminal ATG of the NdeI site represented the presumptive ATG start codon of the pdhA gene. The start codon was assigned by alignment of other pdhA genes and examination of the possible reading frames.

This was used in conjunction with the reverse primer 5'-CCAAGCTTTCTTTAATATCTTCTTTTGCTTG-3 (SEQ ID NO:8) (incorporating a HindIII site) to amplify the front portion of the pdhA(a) gene, using previously described PCR protocols. A PCR product of approx 1 kb was generated, purified and ligated into pUC19 (NEB). The ligation mixture was used to transform *E. coli* JM109 (Stratagene) using standard protocols. Ampicillin-resistant colonies were selected and the contained plasmids were isolated, characterized by restriction analysis before the pdhA fragment was digested with NdeI and HindIII and subcloned into pTMO31 using standard protocols. The final construct in pTMO31 was verified by sequencing, and assigned as pTMO46.

iii) Promoter Fragments and Generation of Final Delivery Constructs

The promoter fragments were then cloned into the pTMO46 construct—preceding the pdhA gene—as KpnI/NdeI fragments. The following promoter regions were chosen for the initial constructs:

TABLE 6

Promoters used in PDH up-regulation and their sources

| Promoter | Source | Oligos used for pcr |
|---|---|---|
| P_ldh(11955) (302 bp) | *G. thermoglucosidasius* NCIMB 11955 lactate dehydrogenase promoter | Fwd CCGGTACCAAAGAGGGCAATCTGAAAGGAAG (SEQ ID NO: 9) Rvs GGCATATGTGTCTGTCATCCTTTCCAAA (SEQ ID NO: 10) |
| P_ldh(11955short) (172 bp) | *G. thermoglucosidasius* NCIMB 11955 lactate dehydrogenase promoter | Fwd CCGGTACCTGATGTAATTGGATGTGATGAT (SEQ ID NO: 11) Rvs GGCATATGTGTCTGTCATCCTTTCCAAA (SEQ ID NO: 12) |
| P_ldh(NCA1503) (171 bp) | *G. stearothermophilus* NCA 1503 lactate dehydrogenase promoter | Fwd CCGGTACCGCGGGACGGGGAGCTGAGTGCTC (SEQ ID NO: 13) Rvs GGCATATGATTCATCCTCCCTCAATATAATG (SEQ ID NO: 14) |
| P_ldh(DSM13240) (165 bp) | *G. stearothermophilus* Strain 10 (DSM13240) lactate dehydrogenase promoter | Fwd CCGGTACCGCGGGACGGGGAGCTAGGCGCC (SEQ ID NO: 15) Rvs GGCATATGTATTCACCTCTTCTTCCTTTTT (SEQ ID NO: 16) |
| P_amy (356 bp) | *G. stearothermophilus* NCA 1503 α-amylase promoter | Fwd CCGGTACCGATCATCCCCCGCTCCCTTCTCC (SEQ ID NO: 17) Rvs AACATATGGCCCTTCCCCCTTAATCAAATG (SEQ ID NO: 18) |
| P_ferrA (156 bp) | *G. stearothermophilus* Strain 10 (DSM13240) ferredoxin promoter | Fwd CCGGTACCTATGTGTAAAAATACAAGAGAG (SEQ ID NO: 19) Rvs GGCATATGAATCGAACCTCCCCAAGTTTAT (SEQ ID NO: 20) |
| P_ferrB (183 bp) | *G. stearothermophilus* Strain 10 (DSM13240) ferredoxin promoter | Fwd CCGGTACCTATGATAACAAAACTAAATAA GATGGATATGTGTAAAAAT (SEQ ID NO: 21) Rvs GGCATATGAATCGAACCTCCCCAAGTTTAT (SEQ ID NO: 22) |

TABLE 6-continued

Promoters used in PDH up-regulation and their sources

| Promoter | Source | Oligos used for pcr |
|---|---|---|
| P_pflX (168 bp) | B. cereus ATCC14579 pyruvate formate lyase promoter | Fwd CCGGTACCAGTTAACACTATATATAGTA (SEQ ID NO: 23)<br>Rvs GGCATATGAATCTCCTCCATTTTTGATTAG (SEQ ID NO: 24) |

Primers were designed to generate these promoter regions from genomic DNA (isolated from *G. thermoglucosidasius* 11955, *G. stearothermophilus* NCA1503, *G. stearothermophilus* DSM13240 and *B. cereus* ATCC14579 as described previously), as KpnI/NdeI fragments, and PCR products were obtained using previously described components and protocols. The purified PCR products were ligated into pTMO23 (pUC19 with the NdeI site deleted) and the ligation mixtures used to transform *E. coli* JM109 (Stratagene) using standard protocols. Ampicillin-resistant colonies were selected and the contained plasmids were isolated, characterized by restriction analysis before the promoter fragments were digested with KpnI and NdeI and subcloned into pTMO46 using standard protocols. The final constructs in pTMO46 was verified by sequencing, and assigned as the plasmids in Table 7.

TABLE 7

Single crossover constructs for PDH up-regulation.

| Vector | Parent | promoter | Selection |
|---|---|---|---|
| pTMO58 | pTMO46 | P_ldh(11955) | amp, kan |
| pTMO59 | pTMO46 | P_ldh(1503) | amp, kan |
| pTMO83, 84 | pTMO46 | P_ldh(short 11955) | amp, kan |
| pTMO93, 94 | pTMO46 | P_ldh(1503 dimer) | amp, kan |
| pTMO97, 98 | pTMO46 | P_ldh(13240) | amp, kan |
| PTMO103, 104 | pTMO46 | P_ferrA | amp, kan |
| pTMO99, 100 | pTMO46 | P_pflX | amp, kan |
| pTMO101, 102 | pTMO46 | P_pflY | amp, kan | iv) Integration of Final Constructs into the *G. thermoglucosidasius* Backbone

TM89 was transformed with the above plasmids using the electroporation protocol described previously. Presumptive integrants were selected as described previously and tested for ethanol and organic acid production in ASYE glucose medium (anaerobic) as well as PDH activity. The results are shown in Table 8.

TABLE 8

| strain | Promoter | OD | Concentration/mM | | | | | U/ml PDH | mg/ml Protein | U/mg protein Specific Activity |
|---|---|---|---|---|---|---|---|---|---|---|
| | | | pyr | glucose | form | acet | EtOH | | | |
| TM226 | P_ldh(13240) | 6.74 | 1.7 | 17.3 | 1.2 | 14.8 | 136.2 | 2.1 | 8.89 | 0.236 |
| TM227 | P_ldh(13240) | 6.31 | 0.7 | 26.2 | 1.0 | 12.6 | 130.7 | 3.5 | 10.32 | 0.339 |
| TM228 | P_pflX | 6.64 | 2.9 | 29.8 | 3.2 | 9.8 | 118.5 | 2.65 | 10.42 | 0.254 |
| TM229 | P_pflX | 5.02 | 4.8 | 24.4 | 0.7 | 12.2 | 119.6 | 0.95 | 7.99 | 0.119 |
| TM230 | P_pflY | 5.02 | 5.7 | 24.3 | 0.3 | 13.3 | 121.1 | 1.2 | 8.3 | 0.145 |
| TM231 | P_pflY | 5.74 | 2.6 | 21.5 | 1.1 | 12.0 | 125.6 | 1.85 | 10.18 | 0.182 |
| TM216 | P_ldh(1503 dimer) | 4.99 | 1.8 | 12.7 | 0.6 | 15.6 | 141.6 | 1.5 | 8.25 | 0.182 |
| TM218 | P_ldh(1503 dimer) | 5.57 | 3.3 | 14.7 | 1.6 | 13.1 | 135.4 | 1.6 | 9.42 | 0.170 |
| TM177 | P_ldh(1503) | 5.45 | 2.9 | 15.2 | 2.9 | 12.6 | 136.9 | 2 | 9.34 | 0.214 |
| TM89 | (control) | *2.2 | 15.2 | 22.4 | 3.0 | 10.0 | 111.0 | 0.09 | 3.39 | 0.027 |

Table 8 PDH assays on 8 hour cultures of new promoter integrants in ASYE (0.5%)+2% glucose The new promoters appear to give relatively high levels of PDH activity, considerably higher than TM89 at this time point (however, the low protein level recorded for TM89 indicates that TM89 may have passed its peak production point). Poor agreement between the two integrants of each promoter makes comparisons of the relative strength of these promoters difficult.

The same strains tested for PDH levels were also tested for ethanol production with increased glucose level and lower aeration, in a further attempt to establish whether any of these new promoters offered any advantages over the original promoter. The results are shown in Table 9 below:

TABLE 9

| | Volume | Promoter | Glucose | EtOH | Pyruvate | Formate | Acetate |
|---|---|---|---|---|---|---|---|
| | | | | | Concentration/mM | | |
| TM226 | Moderate O$_2$ | P__ldh(13240) | | | No growth | | |
| TM227 | Moderate O$_2$ | P__ldh(13240) | | | No growth | | |
| TM228 | Moderate O$_2$ | P__pflX | 46.2 | 154.2 | 0.3 | 0.0 | 19.4 |
| TM229 | Moderate O$_2$ | P__pflX | 55.9 | 133.1 | 0.6 | 0.0 | 21.9 |
| TM230 | Moderate O$_2$ | P__pflY | 56.3 | 133.4 | 0.7 | 0.0 | 21.2 |
| TM231 | Moderate O$_2$ | P__pflY | | | No growth | | |
| TM216 | Moderate O$_2$ | P__ldh(1503 dimer) | 52.9 | 134.2 | 0.4 | 0.0 | 23.9 |
| TM218 | Moderate O$_2$ | P__ldh(1503 dimer) | | | No growth | | |
| TM177 | Moderate O$_2$ | P__ldh(1503) | 58.2 | 130.8 | 0.6 | 0.0 | 24.2 |
| TM89 | Moderate O$_2$ | control | 88.9 | 85.4 | 12.2 | 0.0 | 19.8 |
| TM226 | Low O$_2$ | P__ldh(13240) | 68.8 | 126.5 | 0.9 | 13.8 | 15.3 |
| TM227 | Low O$_2$ | P__ldh(13240) | 104.3 | 54.9 | 23.8 | 19.1 | 4.6 |
| TM228 | Low O$_2$ | P__pflX | 73.7 | 117.3 | 1.4 | 15.8 | 15.1 |
| TM229 | Low O$_2$ | P__pflX | 94.0 | 80.8 | 13.1 | 19.0 | 9.2 |
| TM230 | Low O$_2$ | P__pflY | 106.6 | 52.0 | 26.0 | 19.6 | 9.2 |
| TM231 | Low O$_2$ | P__pflY | 106.5 | 53.8 | 24.0 | 20.0 | 4.9 |
| TM216 | Low O$_2$ | P__ldh(1503 dimer) | 76.4 | 115.4 | 0.9 | 14.9 | 16.3 |
| TM218 | Low O$_2$ | P__ldh(1503 dimer) | 74.6 | 120.2 | 2.2 | 15.5 | 15.0 |
| TM177 | Low O$_2$ | P__ldh(1503) | 64.9 | 133.6 | 0.7 | 13.1 | 16.3 |
| TM89 | Low O$_2$ | control | 109.5 | 51.1 | 25.6 | 20.6 | 2.9 |

Table 9 Investigated the efficacy of new promoters in 3% glucose under two conditions of oxygen limitation.

It became clear that to characterise fully and compare these promoters it was necessary to generate double recombinants, as the instability of the promoter-replacements gave rise to inconsistencies in the above assays. A stable PDH up-regulation mutation was also required in the final organism.

c) Double Crossover PDH Mutants i) Generation of Final Delivery Constructs

Figure 4:
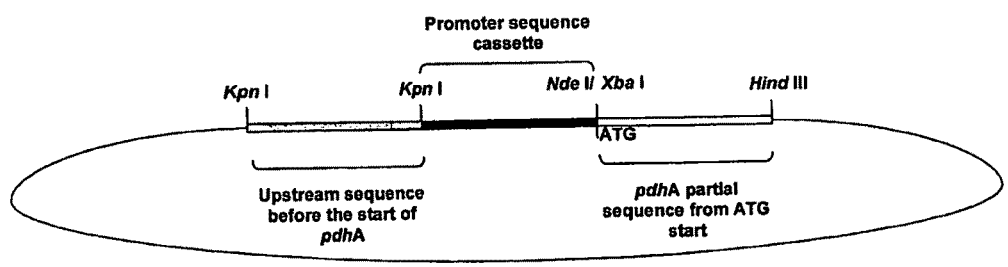
FIG. 4 is a schematic representation of a promoter replacement construct for double-crossover up-regulated PDH mutants.

Stable, double cross-over integrants were generated using a further series of vectors, based on the pTMO58 series in Table 7, in which sequence upstream of the pdhA gene was placed ahead of the promoter fragment, as outlined in FIG. 4. This allowed the excision of the vector sequences in a recombination event and the stable insertion of the replacement promoter ahead of the pdh gene.

For example, a section of sequence preceding the G. thermoglucosidasius 11955 pdh cluster was amplified by PCR, as described previously, to introduce KpnI sites at both ends. This sequence (1072 bp) included 326 bp of the pdf2 gene and the entire intervening open reading frame—the ykaA homologue—but omits the sequence between ykaA and the translation start of pdhA. The purified PCR product was ligated into pUC19 and the ligation mixtures used to transform E. coli JM109 (Stratagene) using standard protocols. Ampicillin-resistant colonies were selected and the contained plasmids were isolated, characterized by restriction analysis before the upstream fragment was digested with KpnI and subcloned into pTMO59 using standard protocols. The final construct was verified by restriction analysis—to establish the orientation of the inserts—and by sequencing, and assigned as pTMO70.

ii) Integration of Final Constructs into the G. thermoglucosidasius Backbone

TM89 was transformed with pTMO70 using the electroporation protocol described previously. Presumptive integrants were selected as described previously and tested for ethanol and organic acid production in ASYE glucose medium (anaerobic) as well as PDH activity.

iii) Generation of Double Cross-Over of P ldh(NCA1503) in TM89

Two primary integrants from the transformation with pTMO70 were selected for serial sub-culture in shaken liquid medium in the absence of kanamycin as described previously. After 3 subcultures, samples were diluted and plated on TGP agar. Plates with suitable numbers of colonies were replica-plated to TGP+kanamycin plates and kanamycin sensitive colonies were picked and purified. These strains were tested for ethanol production in ASYE (0.5%)+2% glucose. Of the sixteen presumptive double-recombinants tested, five (TM179-TM183) gave the desired phenotype (the others appeared identical to the parent TM89). The results are given in Table 10.

TABLE 10

Metabolite Formation in Presumptive Double Cross-Over Mutants.

| Strain | Residual Glucose | Ethanol | Pyruvate | Acetate |
|---|---|---|---|---|
| TM179 | 0.0 | 150.5 | 0.0 | 25.8 |
| TM180 | 0.0 | 152.0 | 0.0 | 21.7 |
| TM181 | 0.0 | 152.8 | 0.0 | 24.3 |
| TM182 | 0.0 | 149.5 | 0.0 | 23.0 |
| TM183 | 0.0 | 146.1 | 0.0 | 24.9 |
| TM89 | 17.4 | 99.0 | 10.7 | 25.3 | d) Checking Presence of the Kan$^R$ Gene from Vector in Double Recombinants

In order to check that the kan$^R$ gene from the vectors used in their construction was no longer present in the double recombinants strains TM89 and TM180, PCR reactions were carried out using primers designed for the kan$^R$ gene, shown in FIG. 3. Control PCR reactions included the use of primers for the pdh gene and preceding region, which would be expected to be present in single-copy in TM89 and TM180. Genomic DNA from five strains (TM15 and LC12.1, the single cross-over integrants from which TM89 and TM180, and TM177) were isolated and used as templates. TM15, LC12.1 and TM177 all show kanamycin resistance and would be expected to bear the vector DNA including the kan$^R$ gene. PCR reactions were run with the conditions and components described earlier with the details of the experiment are given in FIG. 5.

The results show that the single cross-over strains all give a PCR product of the expected size (approx 0.6 kb) with the kan primers, as expected, but there is no PCR product with the kan primers from TM89 or TM180. This indicates that the kan$^R$ gene is not present in these double recombinants, as predicted. The pdh region primers however gave products of the expected size with all five genomic DNAs. The LC12.1 and TM180 genomic DNAs give a product approx 0.2 kb smaller than the other 3 strains, since the P_ldh (NCA1503) replacement insert is smaller than the wild-type sequence.

Example 3

Generation of a Stable PFL Negative Mutant

Figure 5:
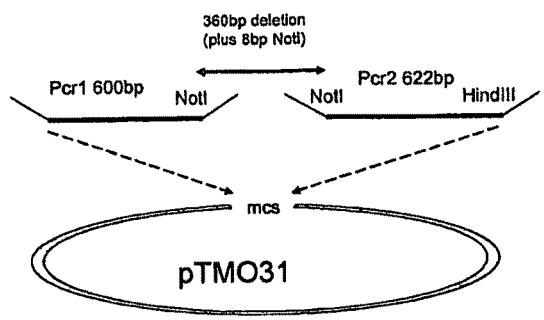
FIG. 5 is a schematic representation of a knock-out construct intended to generate a stable PFL-negative mutant.
Figure 6:
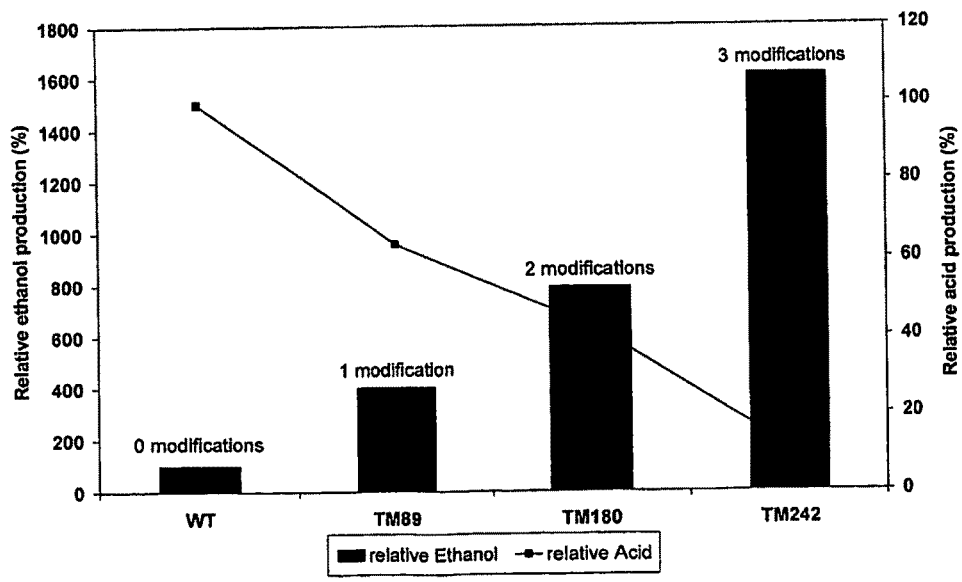
FIG. 6 is a graphic illustration of the elevated ethanol production produced with the mutant microorganisms of the invention.

The PFL knockout vector was constructed in exactly the same manner as the LDH knockout in strategy 2 and is outlined in FIG. 5.

a) PFL Knockout Vector Construction

Degenerate primers 5'-CGTGAAAACGGWGGCG-TYCTTGATATGGATACA-3' (forward SEQ ID NO:25), and 5'-TTCGCACCTGGWGCAAAYGGTTCTCC-3' (reverse SEQ ID NO:26), designed based on sequence homology between known *Bacillus* PFL sequences, were used to amplify a 1.7 kb fragment using genomic DNA from *G. thermoglucosidasius* 11955 as a template. The PCR was carried out as described previously with the purified PCR products ligated into pUC19 (NEB). The ligation mixture was used to transform *E. coli* JM109 (Stratagene) using standard protocols. Ampicillin-resistant colonies were selected and the contained plasmids were isolated, characterized by restriction analysis and sequenced. The resulting plasmid was assigned pTMO95.

A second series of PCR were run with primers to introduce the NotI sites at the 3' end of fragment 3 and the 5' end of fragment 4. In PCR1 primers 5'-CCGGAATTTCACTTC-CCACGGACCAGGTTA-3' (forward SEQ ID NO:27) and 5'-AAGCGGCCGCTATCCAAGAAGGTGGAAACGC-3' (reverse SEQ ID NO:28) were combined with pTMO95 with conditions and components described previously and the purified PCR products ligated into pUC19 (NEB). The ligation mixture was used to transform *E. coli* JM109 (Stratagene) using standard protocols. Ampicillin-resistant colonies were selected and the contained plasmids were isolated, characterized by restriction analysis and sequenced. The resulting plasmid was assigned pTMO105.

In PCR2 primers 5'-AAGCGGCCGCTGCGCGTC-GAATTTGGCGATGA-3' (forward SEQ ID NO:29) and 5'-CCAAGCTTCCGTATACAACGTTAGACGTAA-3' (reverse SEQ ID NO:30) were combined with pTMO95 with conditions and components described previously and the purified PCR products ligated into pUC19 (NEB). The ligation mixture was used to transform *E coli* JM109 (Stratagene) using standard protocols. Ampicillin-resistant colonies were selected and the contained plasmids were isolated, characterized by restriction analysis and sequenced. The resulting plasmid was assigned pTMO107.

Plasmid pTMO107, containing fragment 4, was digested with NotI and HindIII. The resulting fragment (622 bp) was ligated into pTMO105, bearing fragment 3, previously digested with NotI and HindIII. The ligation mixture was used to transform *E. coli* JM109 (Stratagene) using standard protocols. As before ampicillin-resistant colonies were selected and the contained plasmids were isolated and characterized by restriction analysis, to establish the orientation of the inserts. A plasmid (pTMO110) with the expected restriction pattern for the desired construct was identified and verified by sequencing using M13 mp18 reverse and forward primers.

The mutated PFL gene fragment was excised from pTMO110 by digestion with EcoRI and HindIII and the purified fragment was ligated with pTMO31 that had previously been digested with EcoRI and HindIII. The ligation mixture was used to transform *E. coli* JM109 (Stratagene) using standard protocols. Ampicillin-resistant colonies were selected and the contained plasmids were isolated and characterized by restriction analysis, to establish the orientation of the inserts. The resulting plasmid was assigned pTMO111.

b) Single Crossover PFL Negative Mutants

Plasmid pTMO111 was introduced by electroporation into TM89 and TM180 as described previously. Transformants of both strains were grown in liquid culture (2TY+kan12 μg/mL) and plated at very high cell densities on TGP+kan12 μg/mL agar at 68° C. to select for integration as described previously.

Colonies were purified by streaking on TGP+kan12 μg/mL agar at 68° C. and used to inoculate 2TY+kan12 μg/mL seed cultures for production tests, using 10 mL of ASYE (0.5%)+2% glucose in 15 mL Falcon tubes (ie. under low oxygen conditions), conditions which had been shown previously to give measurable levels of formate production by TM89 and TM180. Formate production is not normally seen with higher oxygen levels (see Table 9). The results of testing presumptive integrants of pTMO111 in TM89 and TM180 are shown in Table 11 below.

TABLE 11

| | Concentration/mM | | | | |
|---|---|---|---|---|---|
| | glucose | EtOH | pyruvate | formate | acetate |
| pTMO111/TM89/1.1 | 95.4 | 13.0 | 11.6 | 5.3 | Neg |
| pTMO111/TM89/1.2 | 69.5 | 44.6 | 23.9 | 19.9 | Neg |
| pTMO111/TM89/1.3 | 89.1 | 17.9 | 15.0 | 7.5 | Neg |
| pTMO111/TM89/2.1 | 63.0 | 52.8 | 26.0 | 21.3 | Neg |
| pTMO111/TM89/2.2 | 66.2 | 48.5 | 26.1 | 19.3 | Neg |
| pTMO111/TM89/2.3 | 64.4 | 45.9 | 28.1 | 22.2 | Neg |
| TM89 | 64.7 | 48.2 | 26.4 | 24.7 | Neg |
| TM89 | 63.1 | 51.2 | 27.8 | 26.0 | Neg |
| pTMO111/TM180/1.1 | 13.9 | 177.8 | 0.0 | 0.0 | 0.5 |
| pTMO111/TM180/1.2 | 9.2 | 174.3 | 0.0 | 0.0 | 6.1 |
| pTMO111/TM180/1.3 | 0.0 | 188.6 | 0.0 | 0.0 | 5.8 |
| pTMO111/TM180/1.4 | 0.0 | 191.7 | 0.0 | 0.0 | 5.1 |
| pTMO111/TM180/2.1 | 5.5 | 184.3 | 0.0 | 0.0 | 4.8 |
| pTMO111/TM180/2.2 | 0.0 | 194.4 | 0.0 | 0.0 | 3.9 |
| pTMO111/TM180/2.3 | 8.9 | 186.6 | 0.0 | 0.0 | 4.1 |
| pTMO111/TM180/2.4 | 11.9 | 170.6 | 0.0 | 0.0 | 3.8 |
| TM180 | 48.7 | 94.6 | 1.2 | 15.0 | 11.0 |
| TM180 | 50.2 | 92.6 | 1.2 | 16.1 | 10.7 |

Table 11 pTMO111 presumptive integrants (68° C.) in TM89 and TM180.

The metabolic profile of the TM89 presumptive integrants (Table 11) all looked very similar to TM89 in this test. With the exception of pTMO111/TM89/1.1 and pTMO111/TM89/1.3, which did not grow well, they produced formate at similar levels to TM89 (approximately 20 mM) and had similar levels of other metabolites and similar levels of residual glucose. However, the TM89 presumptive integrants may not be genuine integrants at the pflB locus. Alternatively, it could be that the mutants of TM89 are not stable in these conditions and that the results observed reflect selection of revertants (loop-out of the plasmid), possibly reflecting higher instability of integrants at lower aeration.

The TM180 presumptive integrants look very different. All showed no production of formate, low acetate and very low residual glucose, when compared with the TM180 control. These are presumably genuine integrants at the pflB locus and therefore defective in PFL production.

c) Stable Gene-Replacement PFL Negative Mutants

Primary integrants of both strains (pTMO111 in TM180 and TM89) were used to generate presumptive double cross-overs for gene replacement. Several primary integrants of each strain were serially sub-cultured in shaken liquid media in the absence of kanamycin, then the cultures were serially-diluted, plated on TGP, and replica-plated to TGP with kan (12 μg/mL) to identify Kan$^s$ colonies, as described previously.

When these Kan$^s$ colonies were screened for reduction in formate production four colonies for each host demonstrated a loss of formate production. The metabolic profiles of these isolates are given in Table 12.

TABLE 12

Presumptive stable gene replacement PFL negative mutants in TM89 and TM180

| Strain | Parent | | Concentration/mM | | | | |
|---|---|---|---|---|---|---|---|
| | | | glucose | EtOH | pyruvate | formate | acetate |
| TM236 | TM89 | Moderate O$_2$ | 42.9 | 75.9 | 19.1 | 0.0 | 8.3 |
| TM237 | TM89 | Moderate O$_2$ | 40.7 | 75.9 | 15.4 | 0.0 | 11.6 |
| TM89 | 11955 | Moderate O$_2$ | 73.4 | 43.7 | 22.1 | 22.5 | 1.8 |
| TM236 | TM89 | Low O$_2$ | 99.3 | 5.5 | 12.8 | 0.0 | 0.0 |
| TM237 | TM89 | Low O$_2$ | 100.0 | 5.1 | 12.1 | 0.0 | 0.0 |
| TM244 | TM89 | Low O$_2$ | 99.8 | 4.1 | 10.6 | 0.0 | 0.0 |
| TM245 | TM89 | Low O$_2$ | 101.4 | 3.9 | 10.1 | 0.0 | 0.0 |
| TM89 | 11955 | Low O$_2$ | 73.4 | 43.7 | 22.1 | 22.5 | 1.8 |
| TM240 | TM180 | Low O$_2$ | 5.9 | 173.0 | 0.2 | 0.0 | 5.8 |
| TM241 | TM180 | Low O$_2$ | 2.7 | 174.1 | 0.0 | 0.0 | 5.4 |
| TM242 | TM180 | Low O$_2$ | 0.0 | 175.2 | 0.0 | 0.0 | 8.0 |
| TM243 | TM180 | Low O$_2$ | 0.7 | 175.4 | 0.0 | 0.0 | 5.8 |
| TM180 | TM89 | Low O$_2$ | 48.3 | 85.9 | 1.0 | 18.0 | 12.1 |

The TM89-based PFL mutants TM236 and TM237, were tested in both moderate and low oxygen conditions. With low oxygen levels these two strains grew very poorly. They utilized only a small amount of glucose and produce only a trace (approximately 5 mM) of ethanol. The only significant product seen was pyruvate (approximately 12 mM), with no measurable formate or acetate. However, with increased oxygen their metabolic profile appeared to be more similar to TM89. This phenotype would fit with a PFL knock-out, where PDH expression is too low under low-aeration/anaerobic conditions to effectively replace the PFL role and would explain the phenotype shown by the primary integrants in Table 12, where the presumptive primary integrants of pTMO111 in TM89 appeared similar to TM89. This would explain the poor growth of the PFL mutants under these conditions and provide a strong selection towards reversion to wild-type by homologous recombination. The other presumptive PFL negative mutants of TM89-TM244 and TM245—were isolated from a different primary integrant, but have similar profiles to TM36 and TM37.

The TM180-based PFL mutants TM240, TM241, TM242 and TM243 (TM243 was from a different primary integrant to the other three) show a phenotype similar to that seen with the TM180-based primary integrants in Table 11 (no measurable formate production, higher ethanol and lower acetate when compared with TM180). They are therefore assumed to be stable PFL mutants from gene-replacement.

d) Proof of PFL Gene Replacement

In order to test whether or not the presumptive PFL mutants described above were genuine gene-replacements, a PCR experiment was set up. Genomic DNA was prepared for TM236, TM241, TM242 and TM243. The primers used were SEQ ID NO:25 and SEQ ID NO:26, used to generate the original PFL PCR product from 11955 which provided the PFL sequence for the knock-out design. The PFL sequence used in the PFL knockout construct pTMO111 was all inside of the primer sequences SEQ ID NO:25 and 26 meaning that the sequence is not contained within pTMO111. Thus the knockout construct should not generate a PCR product with these primers, but the gene replacement strains and the wild-type strain should generate a product.

Genomic DNA from the PFL negative gene replacement mutants should give a single PCR product smaller than the wild-type product by 0.4 kb, and carrying a new NotI site.

Using these primers and genomic DNAs, with 11955 genomic DNA and pTMO111 plasmid DNA as controls, it was demonstrated that all four mutants gave a single PCR product of approx 1.3 kb (theoretical 1342 bp), compared with a single product of approximately 1.7 kb from 11955 (theoretical 1694 bp). As expected, no product was obtained with pTMO111. The PCR products from the five strains were gel-purified, digested with NotI and run on an agarose electrophoresis gel. The PCR product from all four PFL negative mutants digested completely to give two products of approximately 0.6-0.7 kb (theoretical: 650 bp and 691 bp), while the 11955 product was not cut by NotI. This test should be definitive, therefore it can be concluded that these four strains are genuine PFL mutants in which the native pfl gene has been replaced (by homologous recombination) with a pfl gene containing a 0.4 kb deletion and a new NotI site.

Xylan Fermentation:

Quick and simple tube culture experiments were run with TM242 in commercially available xylan (Sigma) that had been autoclaved and treated with a variety of hemicellulases. We observed the disappearance of saccharide peaks in HPLC analysis and in further experiments we observed ethanol production—suggesting that the organism not only has the potential to be able to ferment enzyme treated hemicellulose (the ultimate target of commercial lignocellulosic ethanol production) but that this organism is able to utilize the dimers—cellobiose and xylobiose—that require the largest quantity of enzyme and time to degrade to glucose and xylose. This is a significant improvement and advantage over current technology. The results of ethanol production using hemicellulase are shown in Table 13.

TABLE 13

Ethanol production results:

| | Hemicellulase | | | | 24 h | 48 h | % increase 24-48 h |
|---|---|---|---|---|---|---|---|
| | 94 | 95 | 96 | 97 | Ethanol (mM) | | |
| 1 | + | + | − | − | 12.84 | 14.82 | 15.4% |
| 2 | + | + | − | + | 17.5 | 18.83 | 7.6% |
| 3 | − | + | + | + | 45.63 | 49.04 | 7.5% |
| 4 | + | − | + | + | 31.18 | 32.28 | 3.5% |
| 5 | − | − | − | + | 10.07 | 10.43 | 3.6% |
| 6 | − | + | + | − | 16.71 | 33.65 | 101.4% |
| 7 | − | + | − | − | 13.4 | 19.09 | 42.5% |
| 8 | − | − | + | − | 15.6 | 34.18 | 119.1% |
| 9 | − | + | − | + | 25.98 | 31.12 | 19.8% |
| 10 | + | + | + | − | 14.63 | 24.29 | 66.0% |
| 11 | + | − | − | − | 11.14 | 11.82 | 6.1% |
| 12 | − | − | − | − | 4.14 | 4.18 | 1.0% |
| 13 | + | − | + | − | 13.78 | 22.25 | 61.5% |
| 14 | − | − | + | + | 42.01 | 46.68 | 11.1% |
| 15 | + | − | − | + | 13.26 | 15.03 | 13.3% |
| 16 | + | + | + | + | 38.27 | 37.19 | −2.8% |

94 Arabinofuranosidase
95 Arabinofuranosidase
96 Endo-xylanase
97 Xylobiase (beta-xyloxidase)

The mutants 11955 and TM242 were also tested for anaerobic fermentation using different carbohydrates as the carbon source. The results are shown in Table 13.

TABLE 14

Anaerobic Fermentation of 11955 & TM242 on Various Carbohydrates

| | Carbohydrate | Acid Production | | Comments |
|---|---|---|---|---|
| | | 11955 | TM242 | |
| 0 | Control (−ve) | − | − | |
| 1 | Glycerol | ± | ± | |
| 2 | Erythritol | − | − | Erythritol (butane-1,2,3,4-tetraol) is a natural sugar alcohol |
| 3 | D-Arabinose | − | − | |
| 4 | L-Arabinose | + | + | C5 - found in hemicellulose |
| 5 | Ribose | + | + | Aldopentose found in RNA |
| 6 | D-xylose | + | + | C5 - found in hemicellulose |
| 7 | L-xylose | − | − | |
| 8 | Adonitol | − | − | Ribitol or adonitol is a crystalline pentose alcohol (C5H12O5) formed by the reduction of ribose |
| 9 | b-methyl-D-xyloside | − | − | Biomass derived - an inducer of xylanase production |
| 10 | Galactose | − | − | C6 - found in hemicellulose |
| 11 | Glucose | + | + | Can repress xylanases (along with everything else) |
| 12 | Fructose | + | + | |
| 13 | Mannose | + | + | C6 - found in hemicellulose |
| 14 | Sorbose | − | − | Sorbose is a ketose belonging to the group of sugars known as monosaccharides. The commercial production of vitamin C (ascorbic acid) often begins with sorbose |
| 15 | Rhamnose | − | − | It can be classified either as a methyl-pentose or a 6-deoxy-hexose. Rhamnose occurs in nature in its L-form as L-rhamnose (6-deoxy-L-mannose). |
| 16 | Dulcitol | − | − | A member of the mannitol-sorbitol-dulcitol sugar group; isomer of C6H8(OH)6 of sorbitol |
| 17 | Inositol | − | − | Inositol, or cis-1,2,3,5-trans-4,6-cyclohexanehexol, is a cyclic polyalcohol that plays an important role as a second messenger in a cell, in the form of inositol phosphates. It is found in many foods, particularly in cereals with high bran content |
| 18 | Mannitol | + | + | Chemically, mannitol is an alcohol and a sugar, or a polyol; it is an isomer of sorbitol |
| 19 | Sorbitol | + | + | A member of the mannitol-sorbitol-dulcitol sugar group; Isomer of C6H8(OH)6 of dulcitol |
| 20 | a-Methyl-D-Mannoside | − | − | |
| 21 | a-Methyl-D-Glucoside | + | + | |
| 22 | N-Acetyl Glucosamine | + | + | glucosamine + acetic acid, part of bacterial cell wall peptidoglycan |
| 23 | Amygdalin | + | + | glycoside isolated from bitter almonds - rumoured to be a cancer cure |
| 24 | Arbutin | + | + | glycosylated benzoquinone extracted from the bearberry plant genus *Arctostaphylos* |
| 25 | Esculin | + | + | glycoside composed of glucose and dihydroxycoumarin - found in bark extracts |
| 26 | Salicin | + | + | 2-(Hydroxymethyl)phenyl-beta-D-glucopyranoside - closely related to aspirin |
| 27 | Cellobiose | + | + | A disaccharide subunit of cellulose composed of two glucose molecules linked in a β(1?4) bond |
| 28 | Maltose | + | + | a disaccharide formed from two units of glucose joined with an α(1?4) linkage - breakdown of starch/dextrins |
| 29 | Lactose | − | − | a disaccharide that consists of β-D-galactose and β-D-glucose molecules bonded through a β1-4 glycosidic linkage - found in milk |
| 30 | Melibiose | − | − | biomass) |
| 31 | Sucrose | + | + | |
| 32 | Trehalose | + | + | an alpha-linked (disaccharide) sugar found extensively but not abundantly in nature - 2 glucoses joined by a 1-1 alpha bond |
| 33 | Inulin | − | − | Inulins are polymers mainly comprised of fructose units and typically have a terminal glucose - plant storage material |
| 34 | Melazitose | − | − | A nonreducing trisaccharide sugar that can be extracted from the juices of various trees |
| 35 | Raffinose | − | − | Raffinose is a complex carbohydrate, a trisaccharide composed of galactose, fructose, and glucose. It can be found in beans, cabbage, brussels sprouts, broccoli, asparagus, other vegetables, and whole grains |

TABLE 14-continued

Anaerobic Fermentation of 11955 & TM242 on Various Carbohydrates

| | Acid Production | | |
|---|---|---|---|
| Carbohydrate | 11955 | TM242 | Comments |
| 36 Starch | + | + | |
| 37 Glycogen | − | − | |
| 38 Xylitol | − | − | Xylitol, also called wood sugar or birch sugar, is a five-carbon sugar alcohol that is used as a sugar substitute |
| 39 Gentibiose | + | + | |

The microorganism defined herein as TM89 and the plasmid DH 108 pUB 190-ldh have been deposited under NCIMB Accession Nos. 41275 and 41276, respectively. The depository is: NCIMB Ltd, Ferguson Building, Craibstone Estate, Bucksburn, Aberdeen, AB21 9YA, United Kingdom.

The invention claimed is:

1. A thermophilic microorganism modified to permit the increased production of ethanol, wherein a first modification is inactivation of a native lactate dehydrogenase gene and a second modification up-regulates a pyruvate dehydrogenase gene,
- wherein the native lactate dehydrogenase gene is rendered inactive by deletion of at least a portion of the native lactate dehydrogenase gene,
- wherein the second modification is the insertion of a gene promoter from *Geobacillus stearothermophilus* upstream of the pyruvate dehydrogenase gene, wherein the promoter operates under anaerobic conditions, and
- wherein the thermophilic microorganism is *Geobacillus thermoglucosidasius*.

2. The microorganism of claim 1, comprising a third modification, to inactivate the dihydrolipoamide transacetylase gene (EC 2.3.1.12).

3. The microorganism of claim 1, comprising a further modification to inactivate the pyruvate formate lyase (PFL) gene.

4. The microorganism of claim 1, wherein the microorganism does not comprise a restriction system.

5. The microorganism of claim 1, wherein the microorganism forms spores.

6. The microorganism of claim 1, wherein the microorganism is stable in a culture medium comprising up to 30% (w/v) ethanol.

7. The microorganism of claim 1, wherein the microorganism can metabolise cellobiose, xylobiose, and/or starch.

8. The microorganism of claim 1, wherein the microorganism is transformable at high frequency.

9. The microorganism of claim 1, wherein the microorganism grows at a temperature from 40° C.-85° C.

10. The microorganism of claim 1, wherein the microorganism comprises a non-native pyruvate decarboxylase gene.

11. The microorganism of claim 1, wherein the microorganism comprises a non-native alcohol dehydrogenase gene.

12. The microorganism of claim 1, wherein the microorganism does not comprise an integration element in the lactate dehydrogenase gene.

13. A method for the production of ethanol, comprising culturing a thermophilic microorganism under suitable conditions in the presence of a C3, C5 or C6 sugar, or oligomer thereof, wherein the microorganism is modified to permit increased production of ethanol, wherein a first modification is inactivation of a native lactate dehydrogenase gene and a second modification up-regulates a pyruvate dehydrogenase gene, wherein the native lactate dehydrogenase gene is rendered inactive by deletion of at least a portion of the native lactate dehydrogenase gene, wherein the second modification is the insertion of a gene promoter from *Geobacillus stearothermophilus* upstream of the pyruvate dehydrogenase gene, wherein the promoter operates under anaerobic conditions, and wherein the thermophilic microorganism is *Geobacillus thermoglucosidasius*.

14. The method of claim 13, wherein the method is carried out at a temperature of between 40° C.-70° C.

15. The method of claim 14, wherein the temperature is from 52° C.-65° C.

16. The method of claim 13, wherein the microorganism is maintained in a culture at a pH of between 4 and 7.5.

* * * * *